(12) United States Patent  
Wu et al.

(10) Patent No.: US 11,022,623 B2  
(45) Date of Patent: Jun. 1, 2021

(54) SAMPLE TRANSPORT METHOD AND APPARATUS, TEST INSTRUMENT AND COMPUTER-READABLE STORAGE MEDIUM

(71) Applicant: MACCURA MEDICAL INSTRUMENT CO., LTD., Chengdu (CN)

(72) Inventors: Zhongyi Wu, Chengdu (CN); Bingqiang Zhao, Chengdu (CN); Xiangfeng Shen, Chengdu (CN); Hualong Wang, Chengdu (CN); Huailin Wang, Chengdu (CN)

(73) Assignee: MACCURA MEDICAL INSTRUMENT CO., LTD., Chengdu (CN)

( * ) Notice: Subject to any disclaimer, the term of this patent is extended or adjusted under 35 U.S.C. 154(b) by 336 days.

(21) Appl. No.: 16/219,952

(22) Filed: Dec. 14, 2018

(65) Prior Publication Data

US 2019/0187165 A1 Jun. 20, 2019

(30) Foreign Application Priority Data

Dec. 14, 2017 (CN) .......................... 201711341964.2  
Oct. 10, 2018 (CN) .......................... 201811178776.7

(51) Int. Cl.
*G01N 35/04* (2006.01)
*G01N 33/487* (2006.01)

(52) U.S. Cl.
CPC .......... *G01N 35/04* (2013.01); *G01N 33/4875* (2013.01); *G01N 2035/046* (2013.01);
(Continued)

(58) Field of Classification Search
CPC .............. G01N 35/04; G01N 33/4875; G01N 2035/0465; G01N 2035/0491;
(Continued)

(56) References Cited

U.S. PATENT DOCUMENTS 3,724,638 A * 4/1973 Peters .................... B65G 47/82  
                                                                                      198/464.2  
5,972,295 A * 10/1999 Hanawa .......... G01N 35/00603  
                                                                                      422/63

(Continued)

FOREIGN PATENT DOCUMENTS

CN         1912594 A     2/2007  
CN       102023158 A     4/2011  
(Continued)

*Primary Examiner* — Jill A Warden  
*Assistant Examiner* — John McGuirk  
(74) *Attorney, Agent, or Firm* — Syncoda LLC; Feng Ma

(57) ABSTRACT

A sample transport method, applied to a test instrument including a conveyor belt, and a loading platform and a grab position sequentially disposed along a transport direction of the conveyor belt, wherein a plurality of sample holder transport positions are disposed on the conveyor belt; the method including: pushing a first sample holder from the loading platform to a sample holder transport position of the conveyor; when a sample position on the first sample holder moves to the grab position, determining whether the sample position moved the grab position is a target sample position; if so, then determining whether all samples positions on the first sample holder before the target sample holder other than a predetermined number of sample positions have completed testing, wherein the predetermined number is sample position number corresponding to a delay time in outputting information indicating whether a sample needs to be retested.

19 Claims, 9 Drawing Sheets

(52) U.S. Cl.
CPC ........... *G01N 2035/0415* (2013.01); *G01N 2035/0429* (2013.01); *G01N 2035/0465* (2013.01); *G01N 2035/0484* (2013.01); *G01N 2035/0491* (2013.01)

(58) Field of Classification Search
CPC ... G01N 2035/0415; G01N 2035/0429; G01N 2035/0484; G01N 2035/046
See application file for complete search history.

(56) References Cited

U.S. PATENT DOCUMENTS

| | | | | |
|---|---|---|---|---|
| 2010/0159603 | A1* | 6/2010 | Hamada | ............... G01N 35/026 436/47 |
| 2017/0219617 | A1* | 8/2017 | Hirami | ................. G01N 35/026 |
| 2017/0285052 | A1* | 10/2017 | Tatsutani | ............ G01N 35/026 |

FOREIGN PATENT DOCUMENTS

| | | | |
|---|---|---|---|
| CN | 102814816 A | * | 12/2012 |
| CN | 103773833 A | | 5/2014 |

\* cited by examiner

SAMPLE TRANSPORT METHOD AND APPARATUS, TEST INSTRUMENT AND COMPUTER-READABLE STORAGE MEDIUM

CROSS-REFERENCE TO RELATED APPLICATIONS

The present application claims priority to Chinese Patent Application No. 201711341964.2 filed on Dec. 14, 2017, and Chinese Patent Application No. 201811178776.7 filed on Oct. 10, 2018. The disclosures of these applications are hereby incorporated by reference in their entirely.

BACKGROUND

In order to achieve automatic injection of multiple samples, a sample transport apparatus in a test instrument usually employs a conveyor belt to transfer the samples. A sample transport method of a sample transport apparatus is typically as follows: a sample holder holding multiple samples is loaded onto the conveyor belt, and the conveyor belt is controlled to deliver the plurality of samples on the sample holder to arrive in sequence at a sample position (e.g., the sample test position), until the plurality of samples on the sample holder are tested, and then the sample holder is removed from the conveyor belt.

The sample transport apparatus can employ an electric motor to drive the conveyor belt. As an actuator, the motor is one of the key products of mechatronics and is widely used in various automation control systems. During an operation, the motor needs to be reset (e.g., motor zero position calibration). When the motor is reset, an optoelectronic sensor can be used to calibrate the motor zero position and control the stepper motor to achieve the motor position.

SUMMARY

The present disclosure relates to the field of medical device technologies and automation control, and in particular, to a sample transport method and apparatus, test instrument and computer-readable storage medium. In addition, the present disclosure relates to a motor resetting (e.g., returning) control method and apparatus.

The inventors of the present application have recognized that a conventional sample transport apparatus can only transport one sample holder at a time. Only after the sample holder is unloaded from the conveyor belt can the next sample holder be transferred, resulting in a low sample transfer inefficiently.

In a first aspect, an embodiment of the present disclosure provides a sample transport method for a testing instrument.

The sample transport method can be applied to a test instrument including a conveyor belt, and a loading platform and a grab position sequentially disposed along a transport direction of the conveyor belt, wherein a plurality of sample holder transport positions are disposed on the conveyor belt.

The method can include:

pushing a first sample holder from the loading platform to a sample holder transport position of the conveyor;

when a sample position on the first sample holder moves to the grab position, determining whether the sample position moved the grab position is a target sample position, wherein the target sample position is used to determine whether it is needed to pushing a next sample holder continuously on the conveyor belt;

if the sample position moved to the grab position is the target sample position, then determining whether all samples positions on the first sample holder before the target sample holder other than a predetermined number of sample positions have completed testing, wherein the predetermined number is sample position number corresponding to a delay time in outputting information indicating whether a sample needs to be retested;

if all samples positions on the first sample holder before the target sample holder other than the predetermined number of sample positions have completed testing, then determining whether the next sample holder is present on the loading platform; and if the next sample holder is present on the loading platform, then pushing the next sample holder from the loading platform to the next sample holder transport position of the conveyor belt.

In some embodiments, the determining whether the sample moved the grab position is a target sample position includes:

based on number of sample positions that can be accommodated on the sample holder, number of sample positions between the loading platform and the grab position, and the predetermined number, obtaining a target sample position numbering of the target sample position on the sample holder; and based on a position numbering of the sample position moved to the grab position and the target position numbering, determining whether the sample position moved to the grab position is the target sample position.

In some embodiments, the based on number of sample positions that can be accommodated on the sample holder, number of sample positions between the loading platform and the grab position, and the predetermined number, obtaining a target sample position numbering of the target sample position on the sample holder includes:

calculating the target position numbering m of the target sample position on the sample holder by using a formula:

$$m = 2n - j + a - 1$$

where n is the number of sample positions that can be accommodated on the sample holder, and j is a number of sample positions between an end of loading platform toward the grab position and the grab position, a is the predetermined number, wherein m and n are positive integers, j and a are integers greater than or equal to 0, and m satisfies: $0 < m \leq n$.

In some embodiments, the determining whether all samples positions on the first sample holder before the target sample holder other than a predetermined number of sample positions have completed testing includes:

if all the samples positions on the first sample holder before the target sample holder other than a predetermined number of sample positions do not need to be retested or have no sample, then all the samples positions on the first sample holder before the target sample holder other than a predetermined number of sample positions have completed testing;

if any one of the samples positions on the first sample holder before the target sample holder other than a predetermined number of sample positions does not satisfy a condition of no need for retesting or having no sample, then not all the samples positions on the first sample holder before the target sample holder other than a predetermined number of sample positions have completed testing.

In some embodiments, the after said determining whether the sample position moved the grab position is a target sample position, the method further includes:

pausing a movement of the conveyor belt, and grabbing a first sample at the target sample position for testing;

from the first sample completes testing and the target sample position moves to the grab position, until the first sample is returned to the target sample position, resuming the movement of the conveyor belt.

In some embodiments, the pushing the next sample holder from the loading platform to the next sample holder transport position of the conveyor includes:

in a time period after completion of a grabbing operation of the first sample and before an operation of returning the first sample is started, or in a time period after completion of the operation of the returning the first sample and before the conveyor belt resumes the movement, pushing the next sample holder from the loading platform to the next sample holder transport position on the conveyor belt.

In some embodiments, after the first sample completes testing, the method further includes:

receiving a test result of the first sample;

determining whether the test result of the first sample is abnormal;

if the test result of the first sample is abnormal, then after a current sample testing is completed, moving the first sample back to the grab position to retest the first sample.

In some embodiments, the pushing the next sample holder from the loading platform to the next sample holder transport position of the conveyor belt includes:

determining whether the next sample holder transport position is located at an exit position of the loading platform;

if the next sample holder transport position is not located at an exit location of the loading platform, then the next sample holder transport position is moved to the exit position of the loading platform, and from the loading platform the next sample holder is pushed onto the next sample holder transport position of the conveyor belt.

In some embodiments, the test instrument further comprises an unloading platform disposed along a transport direction after the grab position; the method further includes, after said pushing the first sample holder to a sample holder transport position on the conveyor belt from the loading platform:

determining whether all samples on the first sample holder have completed testing;

if all the samples on the first sample holder have completed testing, then moving the first sample holder to an entrance location of the unloading platform and transferring the first sample holder from the conveyor belt to the unloading platform.

In some embodiments, after all samples on the first sample holder have completed testing, the method further includes:

determining whether a next sample holder is present on the conveyor belt;

if the next sample holder is present on the conveyor, proceed to testing of each sample position on the next sample holder, and during the testing of the each sample on the next sample holder, when the first sample holder moves to the entrance location of the unloading platform, moving the first sample holder from the conveyor belt to the unloading platform.

In some embodiments, the after the first sample holder is moved to the unloading platform from the conveyor, the method further includes:

updating a numbering of the next sample holder to the first sample holder.

In some embodiments, the test instrument further comprises, disposed along the transport direction of the conveyor belt between the loading platform and the unloading platform, a preprocessing position, and the method further includes:

obtaining information on the first sample holder when the first sample holder moves to the preprocessing position to thereby guide a grabbing operation at the grab position;

determining whether a sample exists at the sample position when the first sample holder moves to the preprocessing position; and if there is a sample at the sample position, then obtaining basic information required for the testing of the sample.

In another aspect, an embodiment of the present disclosure provides a sample transport apparatus including: a controller configured to configured to control one of the first sample holders being pushed from the loading platform to the to a sample holder transport position of the conveyor;

a first determining portion configured to determine, when a sample position on the first sample holder moves to the grab position, whether the sample position moved the grab position is a target sample position, wherein the target sample position is used to determine whether it is needed to pushing a next sample holder continuously on the conveyor belt;

a second determining portion configured to determine, if the sample position moved to the grab position is the target sample position, then determining whether all samples positions on the first sample holder before the target sample holder other than a predetermined number of sample positions have completed testing, wherein the predetermined number is sample position number corresponding to a delay time in outputting information indicating whether a sample needs to be retested;

a third determining portion configured to determine, if all samples positions on the first sample holder before the target sample holder other than the predetermined number of sample positions have completed testing, then determining whether the next sample holder is present on the loading platform; and the controller is further configured to control, if the next sample holder is present on the loading platform, pushing the next sample holder from the loading platform to the next sample holder transport position of the conveyor belt.

In some embodiments, the first determining portion includes a computation portion configured to determine, based on number of sample positions that can be accommodated on the sample holder, number of sample positions between the loading platform and the grab position, and the predetermined number, obtaining a target sample position numbering of the target sample position on the sample holder; and a determining unit configured to, based on a position numbering of the sample position moved to the grab position and the target position numbering, determine whether the sample position moved to the grab position is the target sample position.

In some embodiments, the second determining portion is configured to determine, if all the samples positions on the first sample holder before the target sample holder other than a predetermined number of sample positions do not need to be retested or have no sample, then all the samples positions on the first sample holder before the target sample holder other than a predetermined number of sample positions have completed testing; and if any one of the samples positions on the first sample holder before the target sample holder other than a predetermined number of sample positions does not satisfy a condition of no need for retesting or having no sample, then not all the samples positions on the first sample holder before the target sample holder other than a predetermined number of sample positions have completed testing.

In some embodiments, the controller is further configured to control:

pausing a movement of the conveyor belt, and grabbing a first sample at the target sample position for testing;

from the first sample completes testing and the target sample position moves to the grab position, until the first sample is returned to the target sample position, resuming the movement of the conveyor belt.

In some embodiments, the controller is further configured to control:

in a time period after completion of a grabbing operation of the first sample and before an operation of returning the first sample is started, or in a time period after completion of the operation of the returning the first sample and before the conveyor belt resumes the movement, pushing the next sample holder from the loading platform to the next sample holder transport position on the conveyor belt.

In some embodiments, the sample transport apparatus further includes:

a receiver configured to receive a test result of the first sample;

a fourth determining portion configured to determine whether the test result of the first sample is abnormal;

the controller is further configured to control, if the test result of the first sample is abnormal, then after a current sample testing is completed, moving the first sample back to the grab position to retest the first sample.

In some embodiments, the sample transport apparatus further includes:

a fifth determining portion configured to determine whether the next sample holder transport position is located at an exit position of the loading platform;

wherein the controller is further configured to control, if the next sample holder transport position is not located at an exit location of the loading platform, moving the next sample holder transport position to the exit position of the loading platform, and from the loading platform the next sample holder is pushed onto the next sample holder transport position of the conveyor belt.

In some embodiments, the test instrument further includes an unloading platform disposed along a transport direction after the grab position; the test instrument further includes a sixth determining module configured to determine, after said pushing the first sample holder to a sample holder transport position on the conveyor belt from the loading platform, whether all samples on the first sample holder have completed testing; wherein the controller is further configured to control, if all the samples on the first sample holder have completed testing, moving the first sample holder to an entrance location of the unloading platform and transferring the first sample holder from the conveyor belt to the unloading platform.

In some embodiments, the apparatus further comprises a seventh determining portion configured to determine, after all samples on the first sample holder have completed testing, whether a next sample holder is present on the conveyor belt; wherein the controller is further configured to control, if the next sample holder is present on the conveyor, proceeding to testing of each sample position on the next sample holder, and during the testing of the each sample on the next sample holder, when the first sample holder moves to the entrance location of the unloading platform, moving the first sample holder from the conveyor belt to the unloading platform.

In some embodiments, the apparatus further comprises an updating portion configured to, the after the first sample holder is moved to the unloading platform from the conveyor, update a numbering of the next sample holder to the first sample holder.

In some embodiments, the test instrument further comprises, disposed along the transport direction of the conveyor belt between the loading platform and the unloading platform, a preprocessing position, and the controller is further configured to: obtain information on the first sample holder when the first sample holder moves to the preprocessing position to thereby guide a grabbing operation at the grab position; determine whether a sample exists at the sample position when the first sample holder moves to the preprocessing position; and if there is a sample at the sample position, then obtain basic information required for the testing of the sample.

In some embodiments, the conveyor belt is equidistantly disposed with a plurality of protrusions adjacent to each other; the portion between the two protrusions forms a sample holder transport position, and the width of the sample holder transport position is less than or equal to the exit width of the loading platform.

In another aspect, a test instrument is provided, which includes the sample transport apparatus.

In another aspect, a computer-readable storage medium is provided, having stored thereon a program that, when executed by a processor, implements the methods described above.

Advantageously, embodiments of the present disclosure employ multiple determining steps, including for example sequentially determining whether the sample position moved to the grab position is the target sample position, whether all other sample positions except the predetermined number of sample positions before the target sample position have completed testing, and whether there is a next sample holder on the loading platform. Through these multiple determining steps, the conveyor belt be loaded with the first sample holder while feeding the next sample holder continuously so long as the multiple determining steps are satisfied. Compared with conventional technologies where only one sample can be transported at a time, the sample transport method in the embodiment can improve the transport efficiency of the sample.

In another aspect, the present disclosure also relates to the field of automation control, and in particular, to the motor reset control method, apparatus, storage medium, and transmission apparatus.

Embodiments of the present disclosure provide a motor reset control method, apparatus, storage medium, and transmission device, which can accurately position a motor reset position.

Concerning the electric motor, the inventors of the present disclosure further recognized that, employing a motor reset blocker, between an optoelectronic trigger to reset the motor and the motor stops moving, there is a certain time difference. Each time motor is reset, there is a position difference between where the optoelectronic sensor is triggered and where the motor stops motion, resulting in a relatively low reset position accuracy.

In some embodiments, a motor reset control method is provided, including:

based on a received motor resetting (e.g., returning) start command, controlling the motor to drive forward in a first direction until a blocker triggers a position limit sensor for a first time, wherein the blocker is disposed at the conveyor belt;

if the first triggered position limit sensor is a first position limit sensor, controlling the motor to drive forward in the first direction until the first position limit sensor is not triggered; and controlling the motor to drive at a first speed less than a preset threshold speed opposite to the first direction, until the blocker triggers the first position limit sensor, the motor stops driving, thereby completing resetting.

In some embodiments, the method further includes:

if the position limit sensor first triggered is not the first position limit sensor, based on a positional relationship between the position limit sensor triggered for the first time and the first position limit sensor, controlling the motor until the blocker triggers the first position limit sensor;

controlling the motor to drive forward in the first direction until the first position limit sensor is not triggered; and controlling the motor to drive opposite to the first direction at the first speed until the blocker triggers the first position limit sensor, and then the motor stops driving.

In some embodiments, the based on a positional relationship between the position limit sensor triggered for the first time and the first position limit sensor, controlling the motor until the blocker triggers the first position limit sensor includes:

if the first position limit sensor is located in a direction forward of the first direction from the first triggered position limit sensor as a starting point, controlling the motor to drive forward in the first direction until the blocker triggers the first position limit sensor;

if the first position limit sensor is located in a direction opposite to the first direction from the first triggered position limit sensor as a starting point, controlling the motor to drive in a opposite direction of the first direction until the blocker triggers the first position limit sensor.

In some embodiments controlling the motor to drive at a first speed less than a preset threshold speed opposite to the first direction includes:

controlling the motor to accelerate to the first speed, and at the first speed and at a constant speed in a direction opposite to the first direction.

In some embodiments, the method further includes:

determining when the motor completes resetting, a position of the blocker is a first position;

receiving the motor resetting start command again, based on the again received motor resetting start command, determining that a position of the blocker is a second position when the motor completes the resetting again; and adjusting the first speed, according to a position difference between the first position and the second position, such that the position difference is smaller than a position difference threshold.

In another aspect, a motor reset control apparatus is provided, including:

a motor reset start portion, configured to start the motor according to the reset command received, control the motor in a first direction forward motion, until the position limit sensor is triggered by the first blocker, which is a blocker on the motor-driven conveyor belt among one or a plurality of blockers;

a first motion control portion configured to, if the first time triggered position limit sensor is the first position limit sensor, control the motor to have a first direction forward motion until the first position limit sensor is no longer triggered;

a second motion control configured to control the motor to have a drive motion at a speed less than a first predetermined speed threshold in a direction opposite to the first direction, until the first position limit sensor is triggered by the blocker, the motor stops moving, such that the motor reset is complete.

In another aspect, a computer-readable storage medium is provided having stored thereon instructions for a computer to execute, to implement the motor reset control method described above.

In another aspect, a sample delivery apparatus is provided, including:

a conveyor belt, a plurality of sample blockers, a motor, and a motor reset control system; wherein the conveyor belt is configured to be driven by the motor, and move a plurality of sample blockers; the plurality of sample blockers are configured to fix the sample positions of the samples on the conveyor belt; a motor reset control system, including: a motor reset start portion, configured to start the motor according to the reset command received, control the motor in a first direction forward motion, until the position limit sensor is triggered by the first blocker, which is a blocker on the motor-driven conveyor belt among one or a plurality of blockers; a first motion control portion configured to, if the first time triggered position limit sensor is the first position limit sensor, control the motor to have a first direction forward motion until the first position limit sensor is no longer triggered; a second motion control configured to control the motor to have a drive motion at a speed less than a first predetermined speed threshold in a direction opposite to the first direction, until the first position limit sensor is triggered by the blocker, the motor stops moving, such that the motor reset is complete.

The motor reset control method, device, storage medium and transmission apparatus according to various embodiments of the present disclosure can have advantages such as that the motor can be stopped at the same position after the motor is reset by the motor motion control and speed control, thereby ensuring the position consistency and accuracy of the motor stop every time the reset is performed.

It is to be understood that, both the foregoing general description and the following detailed description describe only some embodiments by way of example, and are not restrictive of the present disclosure.

BRIEF DESCRIPTION OF THE DRAWINGS

In order to clearly illustrate the various embodiments provided in the present disclosure, the following are drawings that accompany the description of the embodiments.

It is noted that these drawings should be interpreted to serve illustrating purposes only, and that these drawings may represent some, but not all, of embodiments of the present disclosure. For those skilled in the art, other embodiments that are based on the structures as described below and illustrated in these drawings may become apparent. As such, these other embodiments should be interpreted to be contained within the scope of the present disclosure.

In the drawings.

101: conveyor belt; 102: loading platform; 103: grab position; 104: sample holder; 105: unloading platform; 106: preprocessing position; 107: label; 801: first sample holder; 802: next sample holder; 1201: control portion; 1202: first determining portion; 1203: second determining portion; 1204: third determining portion.

DETAILED DESCRIPTION

Descriptions will now be made in detail with respect to some embodiments, examples of which are illustrated in the accompanying drawings. The following description refers to the accompanying drawings in which the same numbers in different drawings may represent the same or similar elements unless otherwise represented. The implementations set forth in the following description of example embodiments do not represent all implementations consistent with the disclosure. Instead, they are merely examples of devices and methods consistent with aspects related to the disclosure as recited in the appended claims.

Some embodiments of the present disclosure provide a sample transport method and device, test instrument and computer-readable storage medium for use in medical field test equipment, such as instrument for measuring blood composition, also known as a blood analyzer, chemical analysis, gene sequencing, etc. Method and apparatus for transporting samples using embodiments of the present disclosure can improve the efficiency of sample transport and increases the speed of sample testing.

Figure 1:
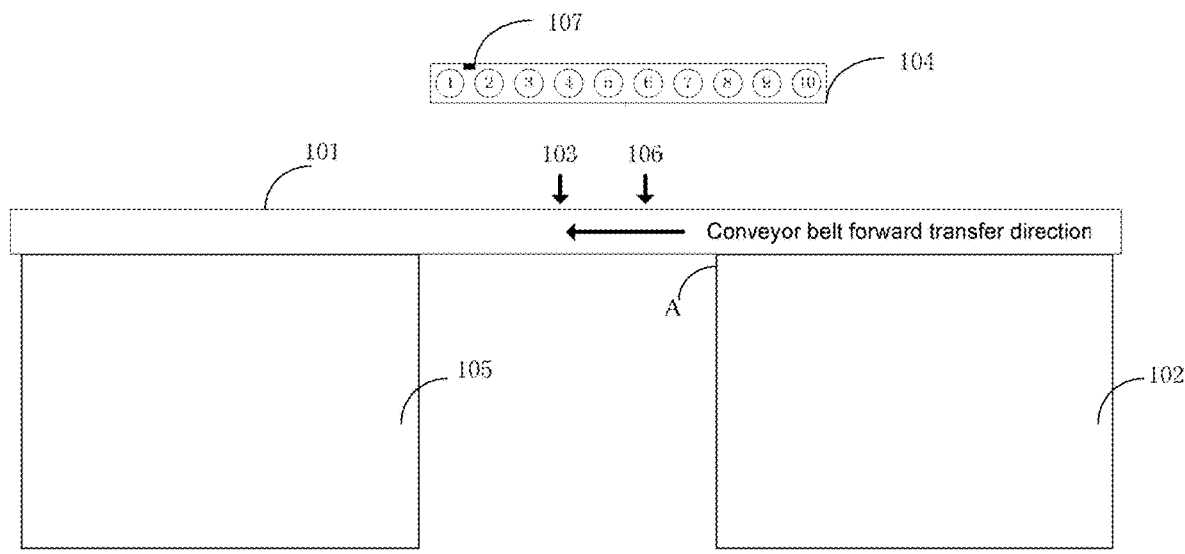
FIG. 1 is a schematic structural diagram of a test instrument according to some embodiments of the present disclosure.

FIG. 1 is a schematic structural view of a test instrument according to an embodiment of the present disclosure. Test instrument in FIG. 1 includes the conveyor belt 101, and the loading platform 102 and the grab position 103 arranged in the conveying direction of the conveyor belt 101. The number of conveyor belts 101 shown in FIG. 1 is one, and the forward direction of the conveyor belt 101 is as indicated by the arrow. Those of ordinary skill in the art will recognize that multiple conveyor belts may be employed, and the forward direction may be defined as other directions, including but not limited to upward direction, slanted direction, etc.

The conveyor belt 101 can transport the sample holder 104 in the forward conveying direction, or the sample holder 104 can be transported in the reverse transport direction. Due to the delay in the sample test results, if the sample is tested to have a result with an abnormality, and when the sample is re-examined, the conveyor belt 101 can be moved in the reverse direction. For example, as a result of a delay in sample test results, if the sample test results are abnormal, if some or all of the samples need to be rechecked, the conveyor belt 101 can reverse its movement direction, and the samples need to be rechecked are moved back to the grab position 103.

According to some embodiments of the present disclosure, a plurality of sample holder transport positions are disposed on the conveyor belt 101, each sample holder transport position can carry one sample holder 104.

In one example, a plurality of protrusions may be disposed on the conveyor belt 101, and adjacent two protrusions can form a sample holder transport position therebetween.

In another example, the plurality of protrusions can be equidistantly disposed.

For example, 6 protrusions can be disposed uniformly, e.g., consecutively, and the conveyor belt 101 can be divided into 6 sample holder transport positions for holding the sample holder 104. Wherein, the width of the sample holder transport position can be less than or equal to the exit width of the loading platform 102. Preferably, the sample holder transport position of the embodiment of the present disclosure has a width equal to the exit width of the loading platform 102 to simplify the control logic in the sample feeding.

The loading platform 102 is used to store a plurality of sample holders 104 to be measured. Illustratively, a pusher assembly is provided on the loading platform 102 to push the sample holder 104 from the loading platform 102 to the conveyor belt 101.

In one example, a sensor can be placed on the loading platform 102 for detecting on the loading platform 102 whether a sample holder 104 is present, to instruction the injection operation of the sample holder 104.

In another example, a blocker can also be placed on the loading platform 102 to prevent the sample holder from abnormally sliding onto the conveyor belt 101.

According to an embodiment of the disclosure, when the empty sample holder transport position is moved to the loading platform 102, to perform the loading operation of the sample holder 104, the loading platform 102 having the above structure is in operation, first the blocker can be moved downward, such that the sample holder 104 can be tested unobstructed in the direction of the conveyor belt 101. Next, pushing, with the pusher assembly, the sample holder 104 to the sample holder transport position. During the process, once the sample holder 104 is detected to be pushed to the sample holder transport position, the pusher assembly is stopped from moving forward, but is then back to the initial position in the opposite direction, while the blocker is up to block the subsequent sample holder from moving in the direction of the conveyor belt 101.

The grab position 103 shown in FIG. 1 is located over the conveyor belt 101. In one example, a sample grabber can be disposed at the position where the grab position 103 is located. When the sample position on the sample holder 104 moves to the grab position 103, the sample grabber grabs the sample from the sample holder and moves the sample to the other places, such as a sample test component (not shown); or, a sample can be grabbed from elsewhere, such as upon the test completed the sample is placed back on the sample holder.

Also shown in FIG. 1 is an unloading platform 105 for recovering samples completed testing from the conveyor belt 101.

In one example, a pusher assembly can be placed at a location corresponding to the unloading platform 105. The sample holder 104 that has been tested is pushed to the unloading platform 105 by the pushing assembly.

In another example, a sensor can also be placed on the unloading platform 105 for detecting whether the sample holder 104 on the loading platform 105 is full. If the sample holder 104 on the unloading platform 105 is detected to be full, the sample feeding is paused.

Also shown in FIG. 1 is a pre-processing position 106 between the loading platform and the unloading platform 105, to pre-process samples on sample holder 104 or the sample holder 104 itself, to obtain basic information of the sample holder 104 or the sample.

In order to obtain the basic information of the sample holder 104 or the sample, in one example, it can be pre-positioned an information acquisition device at the location of the pre-processing position 106 to perform a pre-processing operation. Wherein, the information acquisition device can be a radio frequency reader or a scanner. If the information acquisition device is a scanner, correspondingly a label 107 can be placed on the sample holder 104, and the label 107 includes a unique bar code or quick recognition (QR) code, or other 1-dimensional, 2-dimensional, or 3-dimensional labels that can be scanned, and one can get basic information by scanning the barcode or QR code on the label 107 of the sample holder 104.

With the information acquisition device described above, when the sample holder 104 is moved to the pre-processing position 106, the sample holder 104 can be subjected to a pre-processing operation to guide the grab position 103 for subsequent grabbing operating. It is also possible to perform a pre-processing operation on the sample positions on the sample holder 104, first determining whether the sample positions actually have samples, if there is a sample at the sample position, then the basic information required for the sample testing is obtained.

There are ten sample positions on the sample holder 104 shown in FIG. 1, and each sample position corresponds to one sample to be tested. In one example, the sample to be tested can be loaded into a test tube and set on the sample holder, where multiple circular openings are arranged to place the tube. It will be understood that the number of sample positions on the sample holder 104 is not be limited to 10, and those of ordinary in the art can determine the number of sample positions according to actual test needs.

It should be noted that the loading platform 102, the grab position 103, the unloading platform 105, and the pre-processing position 106 can be fixed relative to the test instrument, and the sample position can be fixed relative to the sample holder 104, i.e., when the sample holder 104 moves with the conveyor belt 101, the sample positions can move synchronously with the conveyor belt 101.

Figure 2:
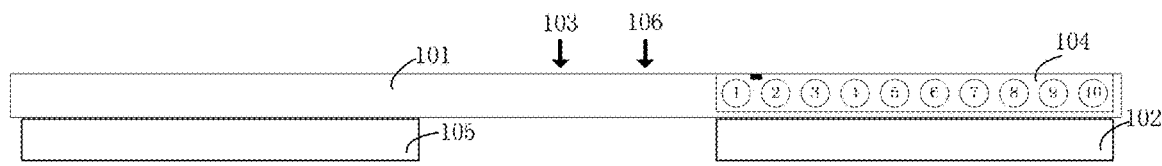
FIG. 2 is a schematic structural diagram of a sample holder when it is in a loading position according to some embodiments of the present disclosure.
Figure 3:
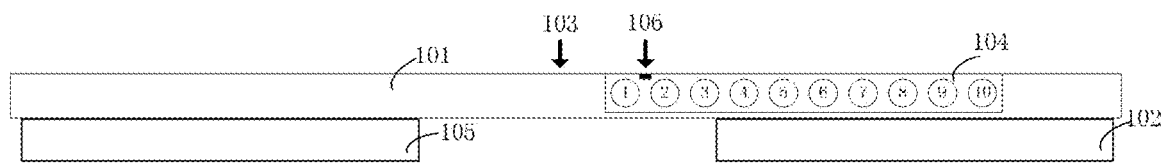
FIG. 3 is a schematic structural diagram of a sample holder when it is in a pre-processing position according to some embodiments of the present disclosure.
Figure 4:
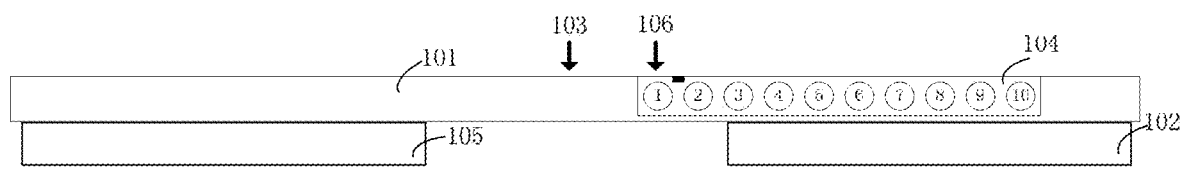
FIG. 4 is a schematic structural diagram of a first sample position in a preprocessing position according to some embodiments of the present disclosure.
Figure 5:
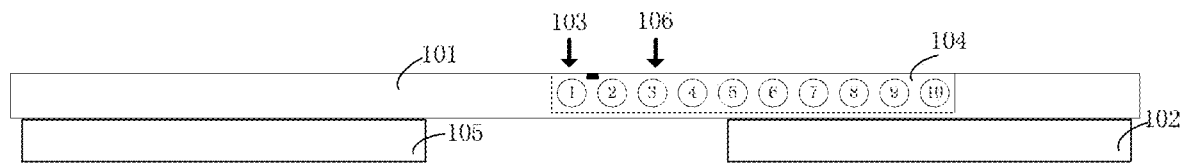
FIG. 5 is a schematic structural diagram of a first sample position in a grab position according to some embodiments of the present disclosure.
Figure 6:
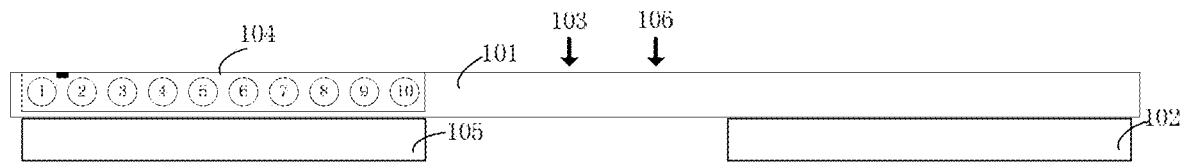
FIG. 6 is a schematic structural diagram of a sample holder when it is in an unloading position according to some embodiments of the present disclosure.

Referring now to FIG. 2 through FIG. 6, the sample feeding portion of the test instrument in the embodiment of the present disclosure can be described. Wherein, FIG. 2 is a structural diagram illustrating a sample holder 104 at the loading platform 102 position according to an embodiment of the present disclosure. That is, the sample holder 104 has just been pushed from the loading platform 102 to the conveyor belt 101 at a sample holder transport position. FIG. 3 is a structural diagram illustrating the sample holder 104 at the pre-processing position 106 according to an embodiment of the present disclosure. FIG. 4 illustrates at the pre-processing position 106 a sample No. 1 provided by an embodiment of the present disclosure. FIG. 5 illustrates the sample No. 1 provided by an embodiment of the present disclosure at the grab position 103. FIG. 6 shows the sample holder 104 being at a position of the unloading platform 105 according to an embodiment of the present disclosure.

Figure 7:
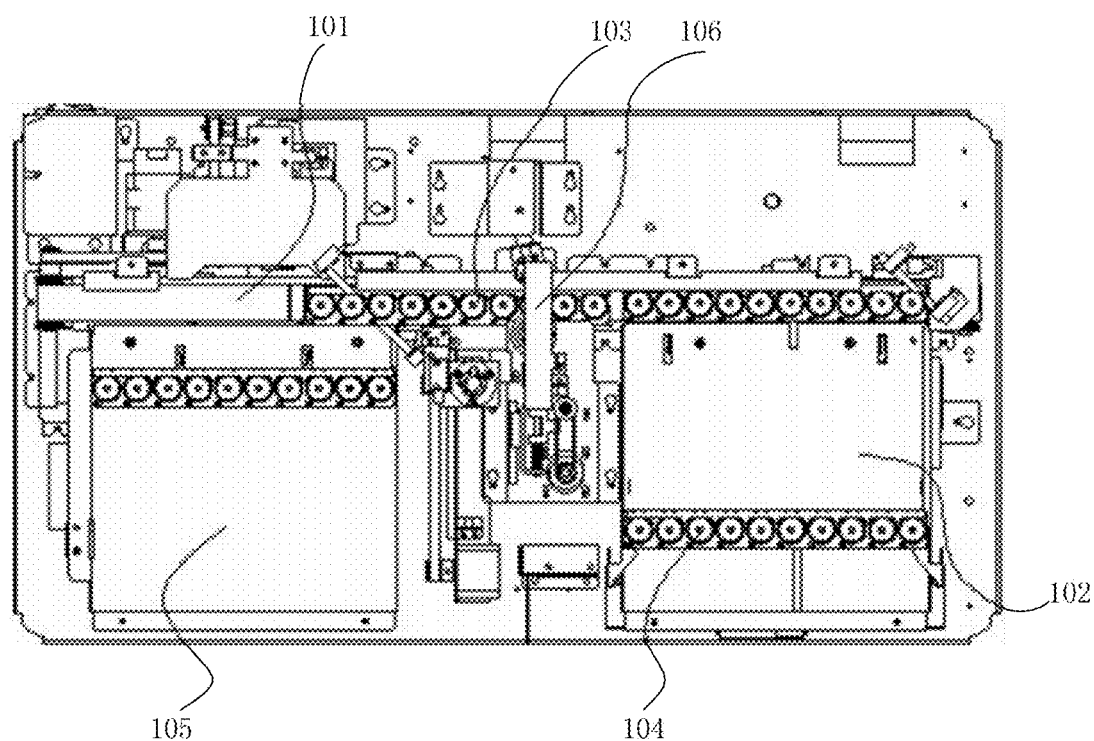
FIG. 7 is a top plan view of a sampling portion of a test instrument according to some embodiments of the present disclosure.
Figure 8:
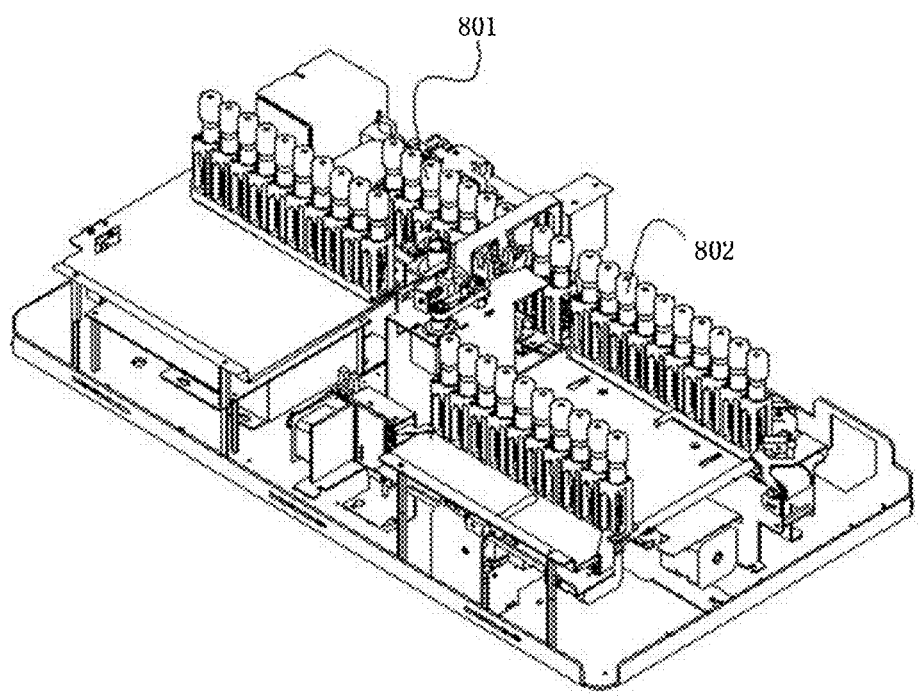
FIG. 8 is a perspective view of a sampling portion of a test instrument according to some embodiments of the present disclosure.

Next, referring to FIG. 7 and FIG. 8 for further understanding of the test instrument in the embodiment of the present disclosure with respect to the structure of the sample feeding portion. FIG. 7 is a top plane view of a sample feeding portion of a test instrument according to an embodiment of the present disclosure. FIG. 8 is a perspective view of a sample feeding portion of a test instrument according to an embodiment of the present disclosure. FIGS. 7 and 8 illustrate the sample holder 104 as accommodating 10 samples.

Loading platform 102, pre-processing position 106, grab position 103, and unloading platform 105 shown in FIG. 7 are sequentially arranged along the conveying direction of the conveyor belt 101. The conveyor belt 101 shown in FIG. 7 can be accommodated with two sample holders 104. The pre-processing position 106 and the grab position 103 are located over the conveyor belt 101, respectively. The loading platform 102 and the unloading platform 105 are respectively located at both ends of the conveyor belt 101, and the outlet width of the loading platform 102, the inlet width of the unloading platform 105 are the same as the width of the sample holder 104 to thereby simplify the control logic of the conveyor belt.

It will be understood that although the number of sample holders 104 that can be accommodated on the conveyor belt 101 shown in FIG. 7 is two, those of ordinary skill in the art can increase the belt length so that the conveyor belt 101 can hold a number of sample holders 104 more than two, which is not limited in the embodiment of the present disclosure.

The positional relationship between the first sample holder 801, the next sample holder 802, and other sample holders is shown in FIG. 8. The sample holder shown in FIG. 8 can hold 10 samples. After the rack 801, the next sample holder 802 is also loaded on the conveyor belt 101. Loading platform 102 has a sample holder 104 that is waiting to be loaded onto the conveyor belt 101. Unloading platform 105 has a sample holder 104 thereon, and all samples on the sample holder 104 have completed testing.

It should be noted that although the pre-processing position 106 and the grab position 103 are respectively shown in FIG. 8 with specific locations, those of ordinary skill in the art can arrange the grab position 103 and the pre-processing position 106 with coincidence settings, or set them separately. In one example, grab position 103 and pre-processing position 106 are also interchangeable, which are not limited by the embodiment of the present disclosure.

Further, a plurality of grab positions 103 and/or multiple pre-processing positions 106 may be set in the test instrument, so that the test instrument can perform test operations on multiple samples at the same time, thereby improving the test instrument delivery efficiency.

Figure 9:
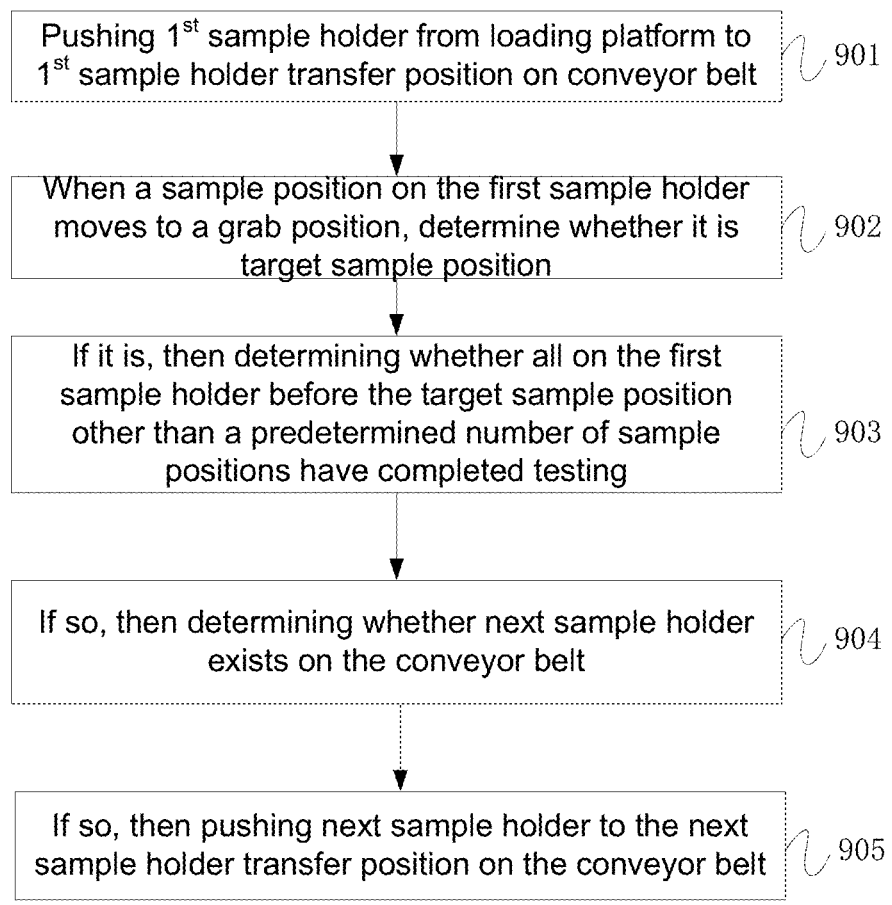
FIG. 9 is a flowchart of a sample transportation method according to some embodiments of the present disclosure.

FIG. 9 is a schematic flow chart of a sample transport method according to an embodiment of the present disclosure. As shown in FIG. 9, the sample transport method can include steps 901 to 905.

In step 901, the first sample holder 801 is pushed from the loading platform 102 to the conveyor belt 101 at a sample holder position.

In one example, the loading platform 102 is provided with a sensor. When the sensor detects the loading platform 102 having the sample holder 104 placed thereon, one of the sample holder transport positions is moved to the exit position of the loading platform 102, to push the first sample holder 801 onto the sample holder transport position.

In step 902, when the sample position on the first sample holder 801 is moved to the grab position 103, it is determined whether the sample position moved to the grab position 103 is the target sample position. Wherein, the target sample position is used to determine whether it is needed to continuously push the next sample holder 802 onto the conveyor belt 101.

In one example, the target position numbering can be based on the number of sample positions that can be accommodated on the sample holder 104, the number of sample positions and the predetermined number between the loading platform 102 and the grab position 103. Based on the numbering of the sample position moved to the grab position 103 and the target sample position numbering, it can be determined whether the sample position moved to the grab position 103 is the target position. If the position number moved to the grab position 103 and the target position number are consistent, then it can be determined that the sample position moved to the grab position 103 is the target sample position. If the position number of the sample position moved to the grab position 103 does not match the target position number, then it can be determined that the sample position moved to the grab position 103 is not a target sample position.

Specifically, the target position number m of the target sample position on the associated sample holder 104 can be calculated by using the following formula:

$$m = n - j + a - 1 \quad (1)$$

wherein n is the number of sample positions that can be accommodated on the sample holder 104, and j is the number of sample positions between an end of the loading platform 102 toward the grab position (see side A in FIG. 1) and the grab position 103, a is a predetermined number, where m and n are positive integers, and j and a are integers greater than or equal to 0, where m satisfies: $0 < m \leq n$. The predetermined number is the same as the output information indicating whether the sample needs to be rechecked The target sample positions on the sample holder 104 is described below with reference to FIGS. 1-8.

Assuming the number of sample positions that can be accommodated on the sample holder 104 is 10, and the delay of the sample test results correspond to a sample position number a=2, and the sample position number j between the loading platform 102 and the grab position 103 is j=4.

When the next sample holder 802 is pushed to the loading platform 102, number 7 sample position on the first sample holder 801 is just transported to underneath the grab position 103. Because the length of the conveyor 101 is fixed, and subject to the limitation of the next sample holder 802, the first sample holder 801 can only advance and cannot be retracted. In addition, the number of sample positions corresponding to the delay of the sample test results is 2, then when the first sample holder 801 has its sample number 7 moved to underneath the grab position 103, test results of at most the first 5 samples can be obtained. Therefore, when the sample position number 7 on the first sample holder 801 is transported to underneath the grab position 103, at least the samples from the first 5 sample positions need to be tested before the next sample holder 802 can have its samples being fed. Therefore, the number of the target sample position on the associated sample holder 104 can be obtained to be 7.

It should be noted that the number of sample positions that can be accommodated on the sample holder 104 in the embodiment of the present disclosure, the number of sample positions between the loading platform 102 and the grab position 10, and the predetermined number are not fixed. Wherein, the number of sample positions that can be accommodated on the sample holder 104, and number of sample positions between the loading platform 102 and the grab position 103 can be adjusted according to the actual situation. The predetermined number can be determined based on the test rate of the test instrument for a single sample.

It can be understood that, in some embodiments of the present disclosure, the target sample position in its associated sample holder 104 is calculated with the formula, which is also not fixed. Those of ordinary skill in the art can, based on the length of the conveyor belt 101, the width of the sample holder transport position, and the width of the loading platform 102, adjust the formula (1) in the embodiment of the disclosure.

In step 903, if the sample position moved to the grab position 103 is the target sample position, then it is determined whether other samples on the first sample holder 801 that are located before the target sample position except for a predetermined number of sample positions have completed the test. Following the example above, that is, on the first sample holder 801, except for a predetermined number of sample positions (2 sample positions in this example), before the target sample position (sample position no. 7), whether the other sample positions (e.g., the first 5 sample positions) have all completed the test.

In one example, if on the first sample holder 801 and located before the target sample position except the predetermined number of sample positions, those sample position all meet the requirements for no retesting, or there is no sample, then all the samples before the target sample position on the sample holder 801 other than the predetermined number of sample positions have complete the test. That is, if the first five sample positions on the first sample holder 801 all meet the need for no retesting, or if no sample is placed, the first 5 samples have all finished testing.

In another example, if among all the other sample positions on the first sample holder 801 and located before the target sample position other than the predetermined number of sample positions there is at least one sample that does not satisfied the condition for no need for retesting, or no sample is placed, then the other sample positions did not complete the test. That is, for any of the first 5 sample positions on the first sample holder 801, if the sample position is not satisfied for no retesting or no sample is placed, then the first 5 samples are not completed for testing.

In step 904, before the target sample position on the first sample holder 801, all other sample positions other than the predetermined number of sample positions are tested, it is determined whether the loading platform 102 has thereon the next sample holder 802.

In step 905, if there is a next sample holder 802 on the loading platform 102, then from the loading platform 102 the next sample holder 802 is pushed onto the next sample holder transport position of the conveyor 101.

In an example, it can be determined whether the next sample holder transport position is located at the loading platform 102 is at an exit position; if the next sample holder transport position is not at the exit position of the loading platform 102, then the next sample holder transport position is moved to the exit position of the loading platform 102, and from the loading platform 102 the next sample holder 802 is pushed onto the next sample holder transport position of the conveyor belt 101.

As described above, some embodiments of the present disclosure employ multiple determining steps, the multiple determining steps include, in an order, determining whether the sample position moved to the grab position 103 is the target sample position, determining, on the first sample holder 801, before the target sample position on the sample holder 801, whether the other sample positions other than the predetermined number of sample positions are all test completed; and determining whether the next sample holder 802 is present on the loading platform 102. Through the plurality of determining steps, the conveyor belt 101 can be loaded with the first sample holder 801, while continue feeding the next sample holder 802 that satisfies the above plurality of determining steps is continuously injected. Therefore, compared with existing technologies where only one sample holder 104 can be transported at a time, that is, only after the sample holder 104 is unloaded from the conveyor belt 101 can the next sample holder 802 be transported, the sample transport in the embodiment of the present disclosure can improve the efficiency of sample delivery.

Figure 10:
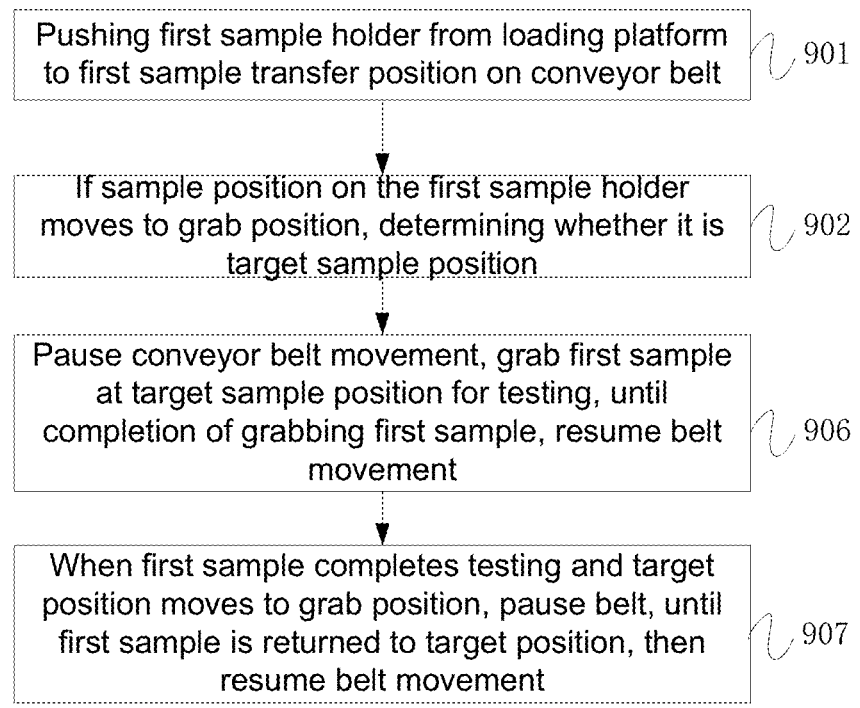
FIG. 10 is a flowchart of a sample transportation method according to some other embodiments of the present disclosure.

FIG. 10 is a flowchart of a sample transport method according to another embodiment of the present disclosure. The difference between FIG. 10 from FIG. 9 is that after the determining step 902 of whether the sample position moved to the grab position 103 is the target sample position, the sample transport method further includes steps 906 and 907 in FIG. 10.

In step 906, the movement of the conveyor belt 101 is suspended and the first sample on the target sample position is captured for testing, until the completion of the grabbing operation of the first sample from the target sample position, and the conveyor belt 101 is resumes its movement.

In step 907, after the first sample test ends and the target sample position moves to the grab position 103, the movement of the conveyor belt 101 is suspended until the first sample is returned to the target sample position, and then the movement of the complex conveyor belt 101 resumes.

That is, when the sample position on the sample holder 104 is moved to the grab position 103, it may need to wait for the sample to be sampled or the sample to be put back, only after the sampling operation or the return operation is completed, the next step can be performed, so that it can be prevented from performing sampling operations or putting back operations, when the conveyor belt 101 moves, it cannot accurately perform the sampling operation or the return operation of the sample.

In one example, after the fetching or grabbing task of the first sample is completed, and before the returning task is started, or after the returning task is completed and before the conveyor belt 101 resumes moving, during the time period, the next step is performed, such as pushing the next sample holder 802 from the loading platform 102 to the next sample holder transport position of the conveyor belt 101.

After the completion of the first sample test, the sample transport method in the embodiment of the present disclosure further includes: receiving the test result of the first sample, determining whether the test result of the first sample is abnormal. If the test result of the sample is abnormal, the first sample is moved again to the grab position after the current sample test ends, to thereby recheck the first sample.

Figure 11:
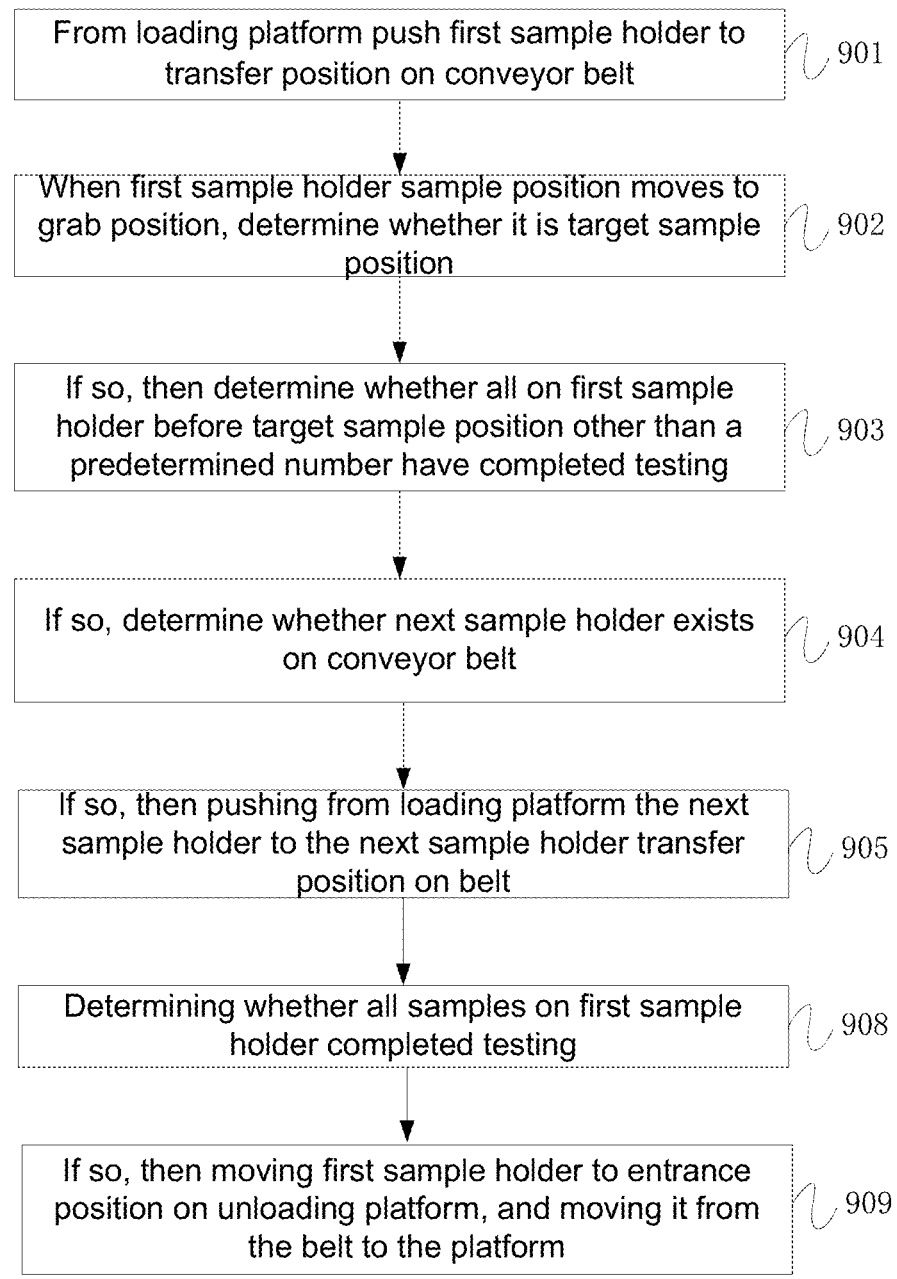
FIG. 11 is a flowchart of a sample transportation method according to yet some other embodiments of the present disclosure.

FIG. 11 is a flowchart of a sample transport method according to yet another embodiment of the present disclosure. FIG. 11 has differences from FIG. 9 including that after step 905 in FIG. 9, the sample transport method further includes step 908 and step 909 in FIG. 11, to perform an unloading operation on the sample holder 104.

In step 908, it is determined whether all samples on the first sample holder 801 have completed testing. That is, all samples on the first sample holder 801 do not need to be re-tested.

In step 909, if all the samples on the first sample holder 801 have been tested, the first sample holder 801 is moved to the entrance position of the unloading platform 105, and passes the first sample holder 801 from the belt 101 onto the unloading platform 105.

In one example, after all samples on the first sample holder 801 have been tested, the first sample holder 801 is directly transferred from the conveyor belt 101 to the unloading platform 105.

In another example, after all samples on the first sample holder 801 have been tested, it is first determined whether there is a next sample holder 802 on the conveyor belt 101, if the conveyor belt 101 has thereon the next sample holder 802, the test of the samples on each sample position on the next sample holder 802 is continued, and during the testing of the samples on the next sample holder 802, when the first sample holder 801 is moved to the unloading platform 105 at the entrance position, the first sample holder 801 is transferred from the conveyor belt 101 to the unloading platform 105, so that the conveyor belt 101 does not need to quickly move the first sample holder 801 to the unloading platform 105, but can be sequentially moved, and the samples on the next sample holder 802 are sequentially tested. At the same time, the first sample holder 801 is moved to the entrance position of the unloading platform 105, thereby improving the test efficiency of the samples.

Further, in order to simplify the control logic of the conveyor belt 101, it may be operated that, on the conveyor belt 101, after the first sample holder 801 is transferred to the unloading platform 105, the numbering of the next sample holder 802 is updated to become the first sample holder 801, but the data of the sample measurement information, status, etc. of the sample holder 104 themselves do not change.

In addition, the sample transport method in the embodiment of the present disclosure further includes, for the sample holder 104 or sample positions on the sample holder 104, a pre-processing step.

In one example, when the first sample holder 801 is moved to the pre-processing position, the sample holder 801 may be subject to the pre-processing to obtain information of the pre-processed position of the sample holder 104, to guide the grabbing operation at the grab position 103.

In another example, when the sample position on the first sample holder 801 is moved to the pre-processing position, it can be determined whether there is a sample on the sample position, and if there is a sample on the sample position, then obtain the sample test basic information needed.

As described above, an information acquisition device such as a radio frequency card reader or a scanner can be disposed at the pre-processing position. For example, a label 107 can be placed on the sample holder 104 or the sample, and the label 107 contains a unique bar code or QR code. By scanning the barcode on the label 107 or the two-dimensional code QR code, information of the sample holder 104 or the sample can be obtained, respectively.

When there is only one sample holder 104 on the conveyor belt 101, the samples can be pre-processed.

For example, it can be determined whether a sample is present or not, then the scan operation can be performed if the sample is present until the sample holder 104 has all of its sample positions pre-processed.

When the number of sample holders 104 on the conveyor belt 101 is greater than one, it is shown in conjunction with FIGS. 1-6 the positions of the sample positions, which can be used for all samples and "next" samples on the "first" sample holder 104, part of the sample holder 104 is pre-processed until all of these sample positions have been pre-processed.

According to an embodiment of the present disclosure, the pre-processing operation and the grab operation may be performed simultaneously, that is, while a sample position has a preprocessing operation, another sample position can have a grab operation. The pre-processing operation and the fetching operation may also be performed separately, that is, when one or more sample positions are all completed with the pre-processing operation, the grab operation is performed separately, which is not limited in the embodiments of the present disclosure.

According to an embodiment of the disclosure, a sample feeder of the test instrument performs a sample transport process including starting, sample holder loading, sample holder pre-processing, sample pre-processing, sample holder grabbing/returning, sample holder unloading, ending, and other processes. Preferably, the prioritization of these processes is: sample grab/return>sample holder loading>sample holder pre-processing>sample pre-processing>sample holder unloading>ending sample feeding process, according to such a priority relationship, the operations can be executed one after the other, and the optimal sample feeding effect can be achieved, for example, there is less waiting time for the sample at the instrument. Of course, those of ordinary skill in the art can also adjust, based on actual conditions, the priority ranking of between the processes, which are not limited in this embodiment of the present disclosure.

As described above, various embodiments of the present disclosure coordinate and manage the sample transportation process, and the processes from the transportation to the testing of the samples are assigned a more reasonable execution timing and execution order, etc., such that the sample feeder of the test instrument can realize fast and automatic sample feeding, reducing the instrument's waiting time for sample acquisition, while speeding up the testing of the sample on the whole apparatus.

Figure 12:
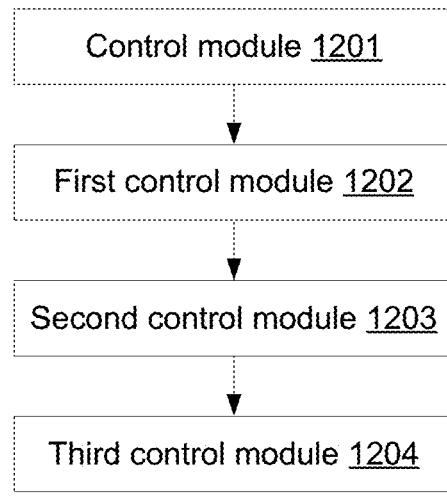
FIG. 12 is a schematic structural diagram of a sample transport device according to some embodiments of the present disclosure.

FIG. 12 is a schematic structural diagram of a sample transport apparatus according to some embodiment of the present disclosure. As shown in FIG. 12, the sample transfer apparatus includes a control module 1201, a first determining module 1202, a second determining module 1203, and a third determining module 1204.

The various device components, units, blocks, or portions may have modular configurations, or are composed of discrete components, but nonetheless may be referred to as "modules" in general. In other words, the "modules" or "units" referred to herein may or may not be in modular forms.

These device components, units, blocks, modules, or portions may be realized with hardware, software, or a combination of hardware and software The control module 1201 is configured to control the first sample holder 801 to be pushed from the loading platform 102 to a sample holder transport position of the conveyor belt 101.

The first determining module 1202 is configured to determine, when the sample position on the first sample holder 801 moves to the grab position 103, whether the sample position moved to the grab position 103 is the target sample position.

Specifically, the first determining module 1202 may include a computing unit and a determining unit. The computing unit is configured to obtain, based on the number of the sample positions that can be accommodated by the sample holder 104, sample number between the loading platform 102 and the grab position 103, and the predetermined number, the target sample position numbering on the sample holder 104. The determining unit is configured to determine, based on the position numbering of the sample position moved to the grab position 103 and the target position numbering, whether the sample position moved to the grab position 103 is the target sample position.

The first determining module 1203 is configured to: if the sample position moved to the grab position 103 is the target sample position, determining, in the first sample holder 801 located before the target sample position except for a predetermined number of sample positions, whether the other sample positions are all tested. If in the first sample holder 801, located before the target sample position, except for a predetermined number of samples, any one of the other sample positions does not meet the standard of no re-examined, or not placed, then it is determined that the other sample positions except the predetermined number of sample positions before the target sample position on the sample holder 801 have not all completed testing.

The third determining module 1204 is configured to determine, in the first sample holder 801 located before the target sample position except for a predetermined number of sample positions, whether the other sample positions are all tested, whether the loading platform 102 has next sample holder 802.

The control module 1201 is further configured to control, if the next sample holder 802 exists on the loading platform 102, the next sample holder 802 being pushed from the loading platform 102 to the next sample holder transport position of the conveyor belt 101.

According to some embodiment of the present disclosures, after it is determined whether the sample position moved to the grab position 103 is a target sample position, the control module 1201 is also used to control the movement pause of the conveyor belt 101 and control the grabbing the first sample on the target sample position for testing, until the first sample is from the target sample position completes grabbing, control conveyor 101 resumes movement; when the first sample has its testing ends and target sample position Moving to the grab position 103, the movement of the control conveyor 101 is suspended until the first sample is placed back to the target sample position, then the conveyor belt 101 is controlled to resume movement. Therefore, it can avoid the conveyor belt 101 moving during the sample grabbing or the return operations, resulting in difficulties executing sample grabbing or returning operations.

In one example, the control module 1201 is also configured to, after the completion of the grabbing operation of the first sample and before the start of the returning operation, control the next sample holder 802 from the loading platform 102 being push up onto the next sample holder transport position of the conveyor belt 101.

Or, in another example, during the period after the return operation is completed and before the conveyor belt 101 resumes movement, the next sample holder 802 is controlled to be pushed from the loading platform 102 to the conveyor belt 101 at the next sample holder transport position.

According to some embodiments of the present disclosure, after the end of the first sample testing, where the sample transport device further includes a receiving module and a fourth determining module, wherein the receiving module is configured to receive the test results of the first sample, and the fourth determining module is configured to determine whether the test results of the first sample are abnormal; the control module 1201 is also configured to control, if the test results of the first sample are abnormal, after the end of the current sample testing, the first sample being moved back to the grab position 103 to retest the first sample.

According to some embodiments of the present disclosure, in order to perform an unloading operation on the sample holder 104, the sample transport device further includes a fifth determining module, wherein the fifth determining module is configured to determine whether the next sample holder transport position is located at the exit position of the loading platform 102; and control the next sample holder 802, if the next sample holder transport position is not located at the exit position of the loading platform 102, being pushed from the loading platform 102 to the next sample holder transport position of the conveyor belt 101.

In one example, the sample transport device further includes a sixth determining module, and the sixth determining module is configured to determine whether all samples on the first sample holder 801 have completed testing; the control module 1201 is further configured to control, if the first sample holder has all its samples completed testing, move the first sample holder 801 to the entrance position of the unloading platform 105, and control the first sample holder 801 to move from the conveyor belt 101 to the unloading platform 105.

In another example, the sample transport device further includes a seventh determining module, and the seventh determining module is configured to determine whether there is a next sample holder 802 on the conveyor belt 101; if there is a next sample holder 802 on the conveyor belt 101, then further control to test each sample position on the next sample holder 802, and during the samples are being tested from the second sample holder 802, when the first sample holder 801 moves to the entrance position of the unloading platform 105, the first sample holder 801 is controlled to move from the conveyor belt 101 to the unloading platform 105. Therefore, it is not necessary for the conveyor belt 101 to move the first sample holder 801 quickly to the unloading platform 105, but rather move sequentially, e.g., while the samples on the next sample holder 802 are being tested, the first sample holder 801 can be moved to the entrance of the unloading platform 105, thereby improving the test efficiency of the samples.

Some embodiments of the disclosure also provide a test instrument. The test instrument includes the sample transfer device as described above. It can be understood that the specific implementations of the sample transfer device described above can be a separate programmable logic controller, or can be integrated into the main controller of the test instrument.

Some embodiments of the disclosure further provide a computer-readable storage medium, on which a program is stored. The program is executed by the processor to implement the sample transport method as described above.

It should be clear that the various embodiments in this specification are described in a progressive manner, each same or similar parts between the embodiments can be referred to each other, and each embodiment focuses on its differences from other embodiments. For device embodiments, the relevant points can be found in the description of the embodiment of the method. Embodiments of the disclosure are not limited to the specific steps and structures in the above description and those shown in the figures. Those skilled in the art can appreciate the spirit of the embodiments of the present disclosure, and make various changes, modifications and additions, or changing the order between the steps. And, for the sake of simplicity and clarity, a detailed description of known method techniques is omitted here.

The functional blocks shown in the block diagrams described above can be implemented as hardware, software, firmware or their combinations. When implemented in hardware, it can be, for example, an electronic circuit, Application-Specific Integrated Circuit (ASIC), appropriate firmware, plug-ins, function cards, etc. When implemented in software, elements of embodiments of the disclosure are programs or code segments that are used to perform the required tasks. The program or code segment can be stored in a machine-readable medium or transmitted by a data signal carried in a carrier wave transmitted on the transmission medium or communication link. "Computer-readable medium" can include those with the ability to store or transmit information, such as any medium of interest. Examples of machine-readable media include electronic circuits, semiconductor memory devices, ROM, flash memory, erasable ROM (EROM), floppy disk, CD-ROM, CD, hard disk, fiber optic media, radio frequency (RF) links, etc. Code segments can be downloaded via the Internet, intranet and other computer network.

In another aspect, a motor resetting control method is provided according to some embodiments of the present disclosure.

Figure 13:
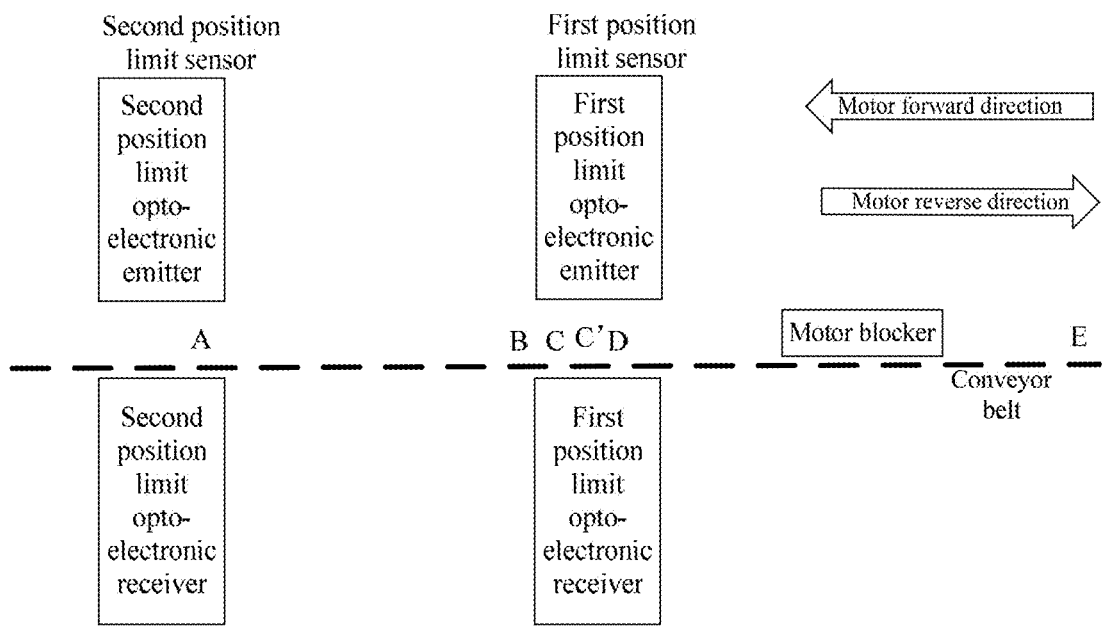
FIG. 13 is a schematic view illustrating an optoelectronic position limiting control of the motor according to some embodiments of the present disclosure.

Referring to FIG. 13, the actuator motor as the equipment may be an object transfer or transport apparatus, which may include a conveyor belt and a blocker disposed thereon. The blocker can be configured to fix the position of the object, sample, or material. The conveyor belt can be coupled through a conveyor belt pulley directly connected to the motor shaft. The motor can be driven to move the blocker on the conveyor belt.

The motor can have two or more operating directions, e.g., clockwise and counterclockwise. One of the operating directions can be selected as the direction of the motor when the motor is reset and started in some embodiments of the present disclosure.

In the following, for the convenience of description, the direction of rotation may be referred to as a first direction, that is the forward direction when the motor is reset and started. Its opposite operating direction may be referred to as a first negative direction opposite to the forward first direction.

In some embodiment, the motor can be a step motor, which can have its rotational speed and acceleration controlled with a pulse frequency, thereby achieving the purpose of motor speed regulation.

As illustrated in FIG. 13, during the driving of the motor (not shown), the movement of the blocker located on a conveyor belt can trigger a position limiting photosensor.

In some embodiments, the position limiting photosensor is a switch configured to control movement of the blocker. As shown in FIG. 13, the position limiting photosensor includes an optoelectronic transmitter and an optoelectronic receiver. In some embodiments, the optoelectronic transmitter can comprises a light-emitting diode, a laser, or other types of light-emitting device, and the optoelectronic receiver can comprise a photoreceiver or photodetector, such as a photodiode.

The following briefly describes the working process of the position limit photosensor. In some embodiments, the emitter of the limit photosensor emits a light signal that is received by the position limit photoreceiver. Without the blocker blocking the position limit optoelectronic receiver, the optoelectronic receiver is not triggered, and light signal transmission continues; during the motion of the motor, when the light signal is blocked by the blocker, the position limit optoelectronic receiver is triggered, and the light signal transmission is OFF.

In some embodiments, when the light signal transmission is OFF, the position limit photosensor may send an OFF-state signal transmitted to the motor control system, which controls the motor to stop in accordance with the OFF state of the signal transmission.

In some embodiments, after the motor stops moving, the motor reset control system can continue to control the motor to move forward in the first direction and in the direction opposite to the first direction.

With continued reference to FIG. 13, in some embodiments of the disclosure, one or more blockers are provided on the conveyor. In the following embodiments, when the motor moves, a position limit photosensor may be triggered by one of the a plurality of blockers.

In some embodiment, the motor reset control system may include one or more position limit sensors, and in the motor reset control system, the sequence and the intervals between these sensors can be pre-recorded.

In connection with FIG. 13, the principles of the motor resetting are described using the example motor reset control system employing only one position limit sensor.

In some embodiments, the motor reset control system includes only one position limit sensor, the position limit sensor can be in a first position limit sensor shown in FIG. 13. The motor reset control method includes:

S01, when the motor reset starts, the motor control system controls the motor to have a forward motion in the first direction until a first position limit sensor is triggered, then the motor stops moving.

As shown in FIG. 13, at position D, the position of the blocker at this time is: motor runs at a first speed in the forward motion direction, a first position limit sensor is triggered by the blocker until the motor stops moving.

In some embodiments, the position of the blocker represented by the position D is different if the first speed of is different during each motor reset.

S02, controlling the motor to move forward in the first direction until the blocker does not trigger the first position limit sensor.

As shown in FIG. 13 in position B, the position of the blocker at this time is as follows: when running at a second speed of the motor in the forward first direction, the blocker happens does not trigger the first position limit sensor, the position of the blocker.

In some embodiments, the position of the blocker represented by position B is different if the second speed of movement is different during each motor reset.

S03, controlling the motor to move in the opposite direction of the first direction until the blocker triggers the first position limit sensor, the motor stops moving, and the motor reset is completed.

Referring to FIG. 13 shown in position C, the position of the blocker at this time is: when the motor runs in the direction opposite to the first direction at a third speed, the blocker just triggered the first position limit photosensor causing the motor to stop, the current position of the blocker.

In this step, the third movement speed is a motor movement speed that is less than the preset speed threshold, and the preset speed threshold is less than or equal to the movement speed of the motor during normal operations.

In some implementations, the object transfer apparatus, such as a sample feeder or sample transport apparatus, can have a plurality of blockers on the conveyor belt, where two adjacent blockers have a space therebetween with a width consistent with a sample holder width, forming a sample holder position.

Because the motor reset drives the belt reset and the blocker reset, it may be needed to ensure that the positions of the adjacent two blockers line up with the sample holder at the entry area when the belt is reset, so as to ensure that the sample holder can be smoothly pushed onto the belt. If the position of the blocker is inaccurate or inconsistent after each motor reset, the sample holder will not be properly fed onto the belt, resulting in malfunction of the instrument or failure to operate properly.

In some embodiments of the present disclosure, in order to ensure the accuracy of the blocker position after each motor reset, by controlling the movement speed of the motor (e.g., the abovementioned third speed), such that the blocker moves in the direction opposite to the first direction starting from a position that does not trigger the first position limit photosensor (e.g., position B), and moves at a very slow and uniform rate to a position that triggers the first position limit photosensor.

For example, the motor is controlled to run at a uniform speed at a third speed of motion, and the blocker moves from the position of the first limit photosensor is not triggered to the position at which the first limit photosensor is triggered. In another example, first accelerate to a third speed of motion and move at a uniform speed to a position that triggers the first position limit photosensor.

In a motor reset control method according to some embodiments of the present disclosure, even if there is a certain time difference between the reset triggering and the stopping of the motor, the blocker does not stop moving immediately as driven by the motor, because the movement speed is sufficiently slow, it can ensure that the error between different blocker positions is sufficiently small each time the motor stops moving, thus ensuring the accuracy and consistency of the position of the blocker after the motor is reset, and ensuring the normal and stable operation of the test instrument.

In a motor reset control method of according to some embodiments of the present disclosure, the motor can start moving at different speeds. The motor reset control system can control the motor from the initial motion speed or the current motion speed, first accelerating to the preset motion speed, for example, the third motion speed, and then move at the preset motion speed until the first position limit optoelectronic sensor is triggered. Therefore, the accuracy and consistency of the position of the blocker after the motor is reset can be ensured to ensure normal and stable operation of the test instrument.

With reference to FIG. 13, using the motor control system comprising a plurality of position limit sensors as an example, the motor resetting principles are described. It should be noted that a "plurality" represents two or more.

In some embodiments of the present disclosure, when the motor control system receives a motor reset start command, the blocker positions are random, not fixed. In order to fix the position of the blocker to be unique after the motor is reset, the relative positions between the first position limit sensor and those other than the first position limit sensor can be determined according to the arrangement order and the separation distance among the plurality of position limit sensors.

S11, the start of the reset, controlling the motor to drive forward in the first direction, determining the first position limit sensor being triggered during the forward motion.

In this step, based on the first triggered position limit sensor, and the relative position between the first triggered position limit sensor and the first position limit sensor, controlling the motor to run until the first position limit sensor is triggered.

S12, based on the relative position between the position limit sensor being first triggered and the first position limit sensor, controlling the motor drive the blocker to the position of triggering the first limit position sensor.

In some embodiments, in a first situation: the first position limit sensor may be located at a position in a first negative direction starting from the position of the first triggered position limit sensor; in a second situation: the first position limit sensor may also be in a position in the first forward direction starting from the first triggered position limit sensor position.

When in the first situation, the motor may be controlled from the position of the first triggered position limit sensor in the first negative direction, until the first position limit sensor is triggered.

When in the second situation, the motor may be controlled to drive in the first forward direction from the position of the first triggered position limit sensor until the first position limit sensor is triggered.

In the first situation, for example, the position C' in FIG. 13, the position of the blocker at this time is: in the first negative motor movement direction at a fourth speed, the blocker just triggered the first position limit photosensor leading to the motor stop, the current position of the blocker.

In this step, if the fourth movement speed is different during each motor reset, the position C' represents different positions of blocker.

In the second situation, taking position D in FIG. 13 as an example, the position of the blocker at this time is: at a fifth moving speed of the motor in the first forward direction, the blocker just triggered the first position limit sensor leading to the motor stop, the current position of the blocker.

In this step, if the fifth movement speed is different during each motor reset, the position D represents different positions of blocker.

Through step S11, the blocker can be controlled to move from any position when the motor starts resetting, to a position that triggers the first limit position sensor. It can be seen that the motor reset control method according to the embodiments of the present disclosure is independent of the position of the blocker at the start of resetting.

Therefore, in some embodiments of the present disclosure, if the motor moves from the first triggered position limit sensor to different directions, until stopping the motion at triggering the first position limit sensor, the positions of the blocker are different (e.g., the position D and position C'). In order to ensure the positional consistency of each reset stop, the motor position should be further adjusted.

Step S12, controlling the motor to move in the negative direction of the first direction until the blocker triggers the first position limit sensor.

As shown in position B in FIG. 13, the position of the blocker at this time is: when the moving speed of the motor is the sixth speed in the first forward direction, the blocker happens not to trigger the first position limit photosensor until the motor stops, the current position of the blocker.

In this step, if the sixth movement speed is different during each motor reset, the position B represents different positions of blocker.

Through step S12, the movement of the motor can be controlled to uniformly adjusted the blocker positions where the first position limit sensor is not triggered.

Step S13, controlling the motor to move in a negative direction in the first direction until the blocker triggers the first position limit sensor, the motor stops moving, and the motor reset is completed.

In position C shown in FIG. 13, the position of the blocker at this time is as follows: when the motor runs in the third speed in the first forward direction, the blocker happens not to trigger the first position limit photosensor stopping the motor movement, the current location of the blocker. Step S13 can be substantially the same as the abovementioned step S03, and therefore is not repeated.

It should be noted that, although both controlling the motor in a direction opposite to the first direction, until the first position limit sensor is triggered, the motor stops moving, position C and position C' of the embodiments described are different in that: the position C is from when the blocker triggers the position limit optoelectronic sensor other than the first position limit photosensor, the blocker moves to triggering the first position limit photosensor and stopping position; the position C' is, the blocker starts from a position that does not trigger the first position limit photosensor, moves at a speed less than the predetermined speed threshold, triggering the first position limit photosensor, the stopping position.

Further, because the predetermined speed threshold is typically less than the normal speed of the motor, each time it resets, it can be ensured that the motor speed can be small enough to ensure that the blocker, when moving from a position that does not trigger the first position limit photosensor to triggering the first position limit optoelectronic sensor and stops, the position of the blocker is substantially the same. Therefore, the position C' has better repeatability and consistency than position C.

Figure 14:
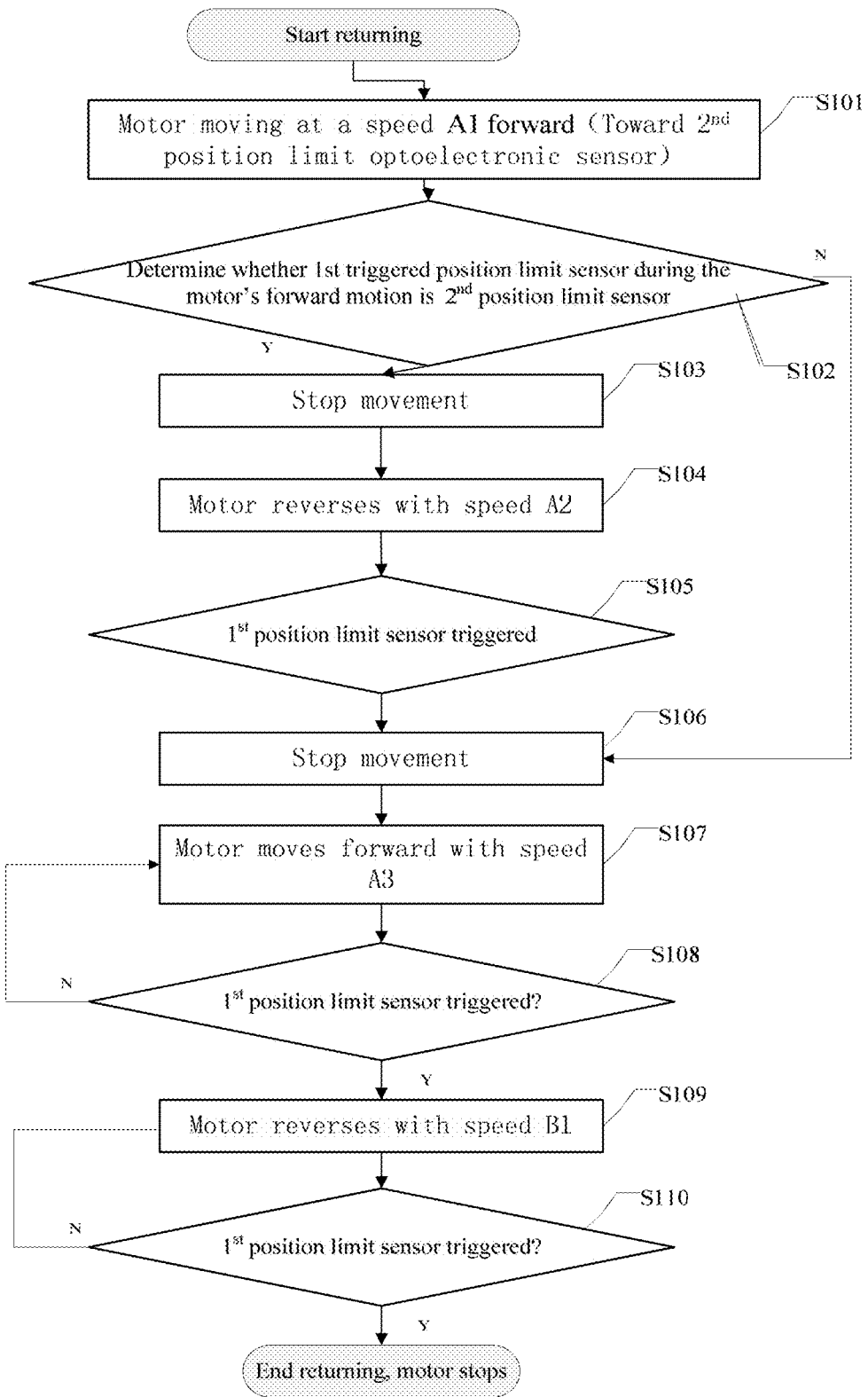
FIG. 14 is a flowchart illustrating a motor resetting control method according to some embodiments of the present disclosure.

Below in connection with FIG. 14, the specific process is described by way of example concerning the motor resetting. FIG. 14 shows a flowchart of a motor reset control method according to some embodiments of the present disclosure.

In these embodiments, the motor reset control system may include, for example, a first position limit sensor and a second position limit sensor, and the first position limit sensor is located in a first negative direction of motion starting from the second limit sensor.

As shown in FIG. 14, in some embodiments, the motor reset control method may include:

Step S101, starting the motor reset, the motor reset control system receives the motor reset signal, and controls the motor to move forward at the speed A1 according to the received motor reset start signal.

Step S102, determining during the motor forward motion, whether the position limit optoelectronic sensor first triggered is the second position limit photosensor.

When the first triggered position limit photosensor is the second limit photosensor, the following steps S103 to S106 are performed;

When the first triggered position limit photosensor is the first position limit photosensor, performing step S106.

Step S103, the motor is controlled to stop moving.

Step S104, the motor is controlled to move in a negative direction at speed A2.

Step S105, determining, during the motor negative direction motion, whether the first limit stop sensor is triggered by the blocker; if the first position limit sensor is not triggered, controlling the motor to continue move in the negative direction, until the first position limit sensor is triggered.

Step S106, the motor stops moving.

Through the above steps it can be seen that, during the motor resetting, when the motor in the forward movement the first triggered position limit sensor is the second position limit photosensor, controlling the motor in a first negative direction, until the first position limit photosensor is trigger and the motor stoops movement. For example, the motor position at this time is the motor position C' described in the above embodiments.

Through the above steps it can be seen that, during the motor resetting, when first triggered position limit optoelectronic sensor during the motor forward motion is the first position limit optoelectronic sensor, and the control motor stops moving. At this time, the motor position is in the position D described in the above embodiments.

Step S107, controls the motor to run at a speed A3 in a forward motion, so that the blocker moves out of the first position limit photosensor.

Step S108: determining whether the first position limit photosensor is triggered. When the first position limit photosensor is continuously triggered, the forward motion of the motor is maintained until the first position limit sensor is not triggered.

As one example, the stepping motor at a speed of forward motion A3, for example, after 100 steps, the blocker no longer triggers the first position limit photosensor, i.e., the blocker has been removed from the first position limit photosensor.

Step S109, controlling the motor at a speed B1 in the negative direction.

Step S110: determining whether the first position limit sensor is triggered. When the first position limit sensor is continuously triggered, the negative movement of the motor is maintained until the first position limit optoelectronic sensor is triggered, and the motor stop finally and stays in the C position described above, the motor reset stops.

In some embodiment, the motor speed may be the motor rotation speed. Motor speeds described above, such as A1, A2 and A3, can have equal values, or different values. For example, the normal speed of the motor running, the normal speed of the motor running may be the speed value set by the user according to the actual application scenario, and is not specifically limited.

The motor reset control method according to some embodiments of the present disclosure, regardless of the motor to clockwise and counterclockwise resetting, regardless of the initial speed of movement and the start and end of the motor speed, after reset start, first it may be determined during a specified direction along the motor movement the first-triggered position limit sensor; based on the first-triggered position limit sensor, the motor is controlled to move to the position where the first position limit sensor is triggered; then the motor is controlled to move to the position of triggering the first position limit photosensor, and then to the position out of range of the first position limit photosensor; and from that position out of range of the first position limit sensor, move in a negative direction at a controllable movement speed less than the predetermined speed threshold until the trigger limit finally stays at the C position, stopping the motor reset. Therefore, consistency and accuracy of the stop position of the motor blocker can be maintained for each reset.

Figure 15:
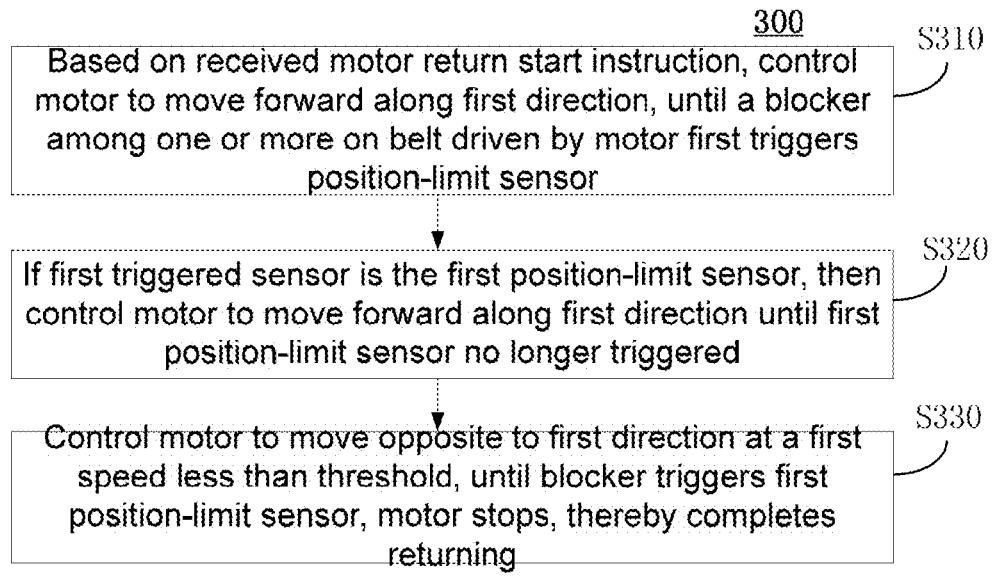
FIG. 15 is a diagram illustrating a method of controlling the motor resetting according to some embodiments of the present disclosure.

FIG. 15 is a diagram illustrating a motor control method according to the reset some other embodiments of the present disclosure. As shown in FIG. 15, in one embodiment, the motor reset control method 300 can include:

Step S310, based on the received motor reset start command, controlling the motor to move in a forward motion in the first direction, until a blocker on a motor driven conveyor belt triggers a position limit photosensor for the first time, the blocker being one or more blockers on the conveyor belt.

In some embodiment, step S310 may specifically include:

based on the received reset start command, controlling the motor to run at a first speed in a first direction that is the forward motion.

Step S320, if the first triggered position limit sensor is the first position limit sensor, then controlling to motor to move in the first direction until the first position limit sensor is not triggered.

Step S330, controlling the motor to move in a negative direction of the first direction at a first speed less than the preset speed threshold, until the blocker triggers the first position limit sensor, and the motor stops moving to complete the reset of the motor.

In some embodiments, controlling the motor to move in a negative direction of the first direction at the first speed comprises:

controlling the motor to accelerate to the first speed, and at a constant first speed in a direction opposite to the first direction.

In some embodiments, the motor reset control method 300 may further include:

step S340, if the first triggered limit sensor is not the first position limit sensor, according to the positional relationship between the first triggered position limit sensor and the first position limit sensor, the motor is controlled to move until the blocker triggers the first position limit sensor;

In some embodiment, step S340 may include:

step S341, if the first position limit sensor is located in the first direction forward direction of the first-triggered position limit sensor, the control motor moves forward in the first direction until the stop triggers the first position limit sensor;

step S342, if the first position limit sensor is located in the first direction negative direction of the first-triggered position limit sensor, the control motor moves in the negative direction of the first direction until the blocker triggers the first position limit sensor.

Step S350, controlling the motor to move forward in the first direction until the first position limit sensor is not triggered;

Step S360, controlling the motor to move in a negative direction of the first direction at the first speed until the blocker triggers the first position limit sensor, and the motor stops moving, wherein the first speed is less than the speed threshold.

In some embodiments of the present disclosure, the motor reset control method 300 may further include:

Step S370, determining that the position of the blocker is the first position when the motor completes resetting;

Step S371, receiving the motor reset start command again, based the motor reset start command received again, determining that the position of the blocker is the second position when the motor completes the reset again;

Step S372, based on a difference between the first position and the second position, adjusting the first velocity, such that the position difference is smaller than the position difference threshold.

In this step, if the position of the blocker is different after each reset, the first speed or the adjusted speed threshold may be adjusted according to different blocker positions after each reset to precisely control the position of the blocker after each reset.

The motor reset control method according to some embodiments of the present disclosure, regardless of the motor to clockwise and counterclockwise reset, based on the reset start time of starting the initial direction of motion and speed of the movement speed of the motor, after the motor reset it can be guaranteed that the blocker may stay at the same position, thereby realizing for each reset, the motor blocker stops position accuracy and consistency.

Figure 16:
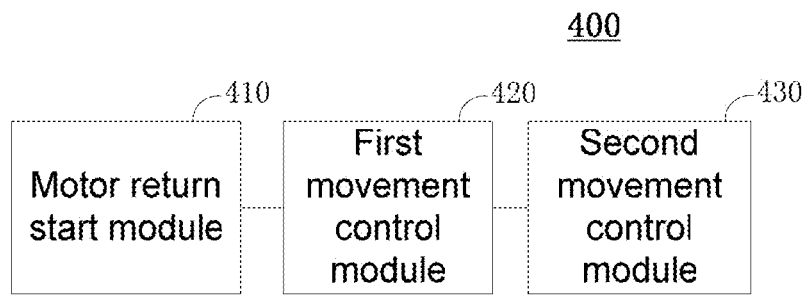
FIG. 16 is a schematic structural diagram of a motor provided in the reset control apparatus according to some embodiments of the present disclosure.

FIG. 16 is a schematic structural diagram of a motor reset control device according to some embodiment of the disclosure. As shown in FIG. 16, the motor reset control device 400 includes:

Motor reset initiation module 410, for starting the motor according to the reset command received, controls the motor in a first direction, a forward motion until the blocker first triggers a position limit sensor, the blocker being any one of one or more of blocks on the conveyor belt.

In some embodiment, the motor reset start module 410 in particular, according to the received start command reset, controls the forward motion of the motor in a first direction, specifically further configured to: start the motor in accordance with the reset start command received, controls the motor to the first speed moving forward in the first direction.

A first motion control module configured to, if the first triggered position limit sensor is the first position limit sensor, control the motor in a forward motion direction until the first position limit sensor is not triggered.

A second motion control module, for controlling the motor to less than a preset speed threshold value, a first speed in a direction opposite to the first direction, until the blocker triggers the first position limit sensor, the motor stops moving, such that the motor reset is complete.

In some embodiments, the motor reset control device 400 may further include:

the third motion control module, configured to control the motor motion according to the positional relationship between the first triggered position limit sensor and the first position limit sensor if the first-triggered position limit sensor is not the first position limit sensor, until the blocker triggers the first position limit sensor;

a fourth motion control module, configured to control the motor to move forward in the first direction until the first position limit sensor is not triggered;

the second motion control module is further configured to control the motor to move in a negative direction of the first direction at a first speed less than the preset speed threshold until the blocker triggers the first position limit sensor, and the motor stops moving, wherein the first speed is less than the speed threshold.

In some embodiment, the fourth motion control module includes:

a forward motion unit, configured to control the motor to move forward in a first direction if the first position limit sensor is located in a first direction forward direction of the first-triggered limit sensor, until the blocker triggers the first position limit sensor;

a reverse motion unit, configured to control, if the first position limit sensor is located in a negative direction of the first direction starting from the first-triggered position limit sensor, the motor in a direction opposite to the first direction, until the blocker triggers first the first position limit sensor.

In some embodiments, the motor reset control device 400 may further include:

a first blocker position determining module, configured to determine that the position of the block is the first position when the motor completes resetting;

a second blocker position determining module, configured to receive the motor reset start command again, and according to the motor reset start command received again, determining that the position of the block is the second position when the motor completes the reset again;

movement speed adjustment module, in accordance with the difference between the first position and the second position, adjusting the first speed, such that the position of the position difference is smaller than a threshold difference.

It is to be understood that the disclosure is not limited to the specific configurations and processes described in the above embodiments and illustrated in the drawings. For the convenience and brevity of the description, a detailed description of known methods is omitted here, and the specific working process of the systems, the modules and the units described above may be referred to the corresponding process in the foregoing method embodiments, and details are not described herein again.

Figure 17:
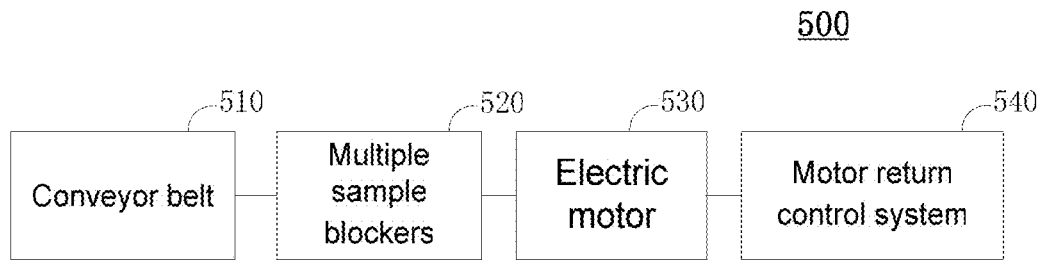
FIG. 17 shows a schematic structural view of a sample transfer device according to some embodiment of the present disclosure.

FIG. 17 shows a schematic structural view of a sample transfer apparatus according to some embodiments of the present disclosure. As shown in FIG. 17, in some embodiments, the sample delivery, transfer or transport device 500 can include:

conveyor belt 510, multiple sample blockers 520, motor 530, and motor reset control system 540.

Wherein the plurality of sample blockers are located on the conveyor belt and the distances between two adjacent ones of the plurality of sample blockers are equal.

The conveyor belt 510 is configured to drive the movement of the plurality of sample blockers driven by the rotation of the motor;

The plurality of sample blockers 520 are configured to fix the sample positions on the conveyor belt;

Motor reset control system 530, for starting the motor according to the reset command received, controlling the motor in a first direction, a forward motion until the blocker first triggers a position limit sensor; if the first-triggered position limit sensor is the first position limit sensor, controlling the motor to run in a forward motion direction until the first position limit sensor is not activated; control the motor to run in a predetermined speed less than a threshold speed moves in a negative direction of the first direction until the blocker triggers the first position limit sensor, and the motor stops moving, to cause the motor to complete the resetting.

In some embodiments of the present disclosure, the motor control system may perform the reset control method in the above embodiments in conjunction with FIG. 13 through FIG. 15, and will not be repeated herein.

A sample transfer device according to some embodiments of the present disclosure can be applied to a feeder for sample analysis. As one example, in the sample analyzer of the feeder, the conveyor belt is connected to the motor shaft, for example, a plurality of sample blockers are disposed on the conveyor belt, two adjacent sample blockers having a distance therebetween may be the width of a sample holder. As a specific example, the sample analyzer can be glycinate protein analyzer, etc., and the specific sample type is not specifically limited in the embodiments of the present disclosure.

In some embodiments of the present disclosure, if two adjacent sample blockers have a sample holder placed therebetween, because the motor reset drives the belt position reset, if during the reset each time the motor position is inaccurate, will result in the sample tube cannot be fed to the belt properly. According to the motor reset control method of some embodiments of the disclosure, the motor reset position can be accurately positioned, so that the position of the sample blocker staying in the reset process can be aligned with the sample holder of the entry area during the reset process, and the sample holder can be smoothly pushed in onto the belt.

In the sample transfer device according to various embodiments of the present disclosure, when the motor is reset clockwise and counterclockwise, respectively, the motor can be stopped at the same position, and the consistency and accuracy of the motor position after each reset are ensured. The reset operation can be performed without determining the specific positions of the blockers. In the sample analyzer sampler feeder, the sample holder pushing action success rate can be greatly increased.

The terms "first" and "second" are used for descriptive purposes only and are not to be construed as indicating or implying a relative importance or implicitly indicating the number of technical features indicated. Thus, elements referred to as "first" and "second" may include one or more of the features either explicitly or implicitly. In the description of the present disclosure, "a plurality" indicates two or more unless specifically defined otherwise.

In the present disclosure, the terms "installed," "connected," "coupled," "fixed" and the like shall be understood broadly, and may be either a fixed connection or a detachable connection, or integrated, unless otherwise explicitly defined. These terms can refer to mechanical or electrical connections, or both. Such connections can be direct connections or indirect connections through an intermediate medium. These terms can also refer to the internal connections or the interactions between elements. The specific meanings of the above terms in the present disclosure can be understood by those of ordinary skill in the art on a case-by-case basis.

In the description of the present disclosure, the terms "one embodiment," "one implementation," "some embodiments," "some implementations," "example," "specific example," or "some examples," and the like may indicate a specific feature described in connection with the embodiment or example, a structure, a material or feature included in at least one embodiment or example. In the present disclosure, the schematic representation of the above terms is not necessarily directed to the same embodiment or example.

Moreover, the particular features, structures, materials, or characteristics described may be combined in a suitable manner in any one or more embodiments or examples. In addition, various embodiments or examples described in the specification, as well as features of various embodiments or examples, may be combined and reorganized.

In some embodiments, the control and/or interface software or app can be provided in a form of a non-transitory computer-readable storage medium having instructions stored thereon is further provided. For example, the non-transitory computer-readable storage medium may be a ROM, a RAM, a CD-ROM, a magnetic tape, a floppy disk, optical data storage equipment, a flash drive such as a USB drive or an SD card, and the like.

Implementations of the subject matter and the operations described in this disclosure can be implemented in digital electronic circuitry, or in computer software, firmware, or hardware, including the structures disclosed herein and their structural equivalents, or in combinations of one or more of them. Implementations of the subject matter described in this disclosure can be implemented as one or more computer programs, i.e., one or more portions of computer program instructions, encoded on one or more computer storage medium for execution by, or to control the operation of, data processing apparatus.

Alternatively, or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them.

Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, drives, or other storage devices). Accordingly, the computer storage medium may be tangible.

The operations described in this disclosure can be implemented as operations performed by a data processing apparatus on data stored on one or more computer-readable storage devices or received from other sources.

The devices in this disclosure can include special purpose logic circuitry, e.g., an FPGA (field-programmable gate array), or an ASIC (application-specific integrated circuit). The device can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The devices and execution environment can realize various different computing model infrastructures, such as web services, distributed computing, and grid computing infrastructures.

A computer program (also known as a program, software, software application, app, script, or code) can be written in any form of programming language, including compiled or interpreted languages, declarative or procedural languages, and it can be deployed in any form, including as a standalone program or as a portion, component, subroutine, object, or other portion suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more portions, sub-programs, or portions of code). A computer program can be deployed to be executed on one computer or on multiple computers that are located at one site or distributed across multiple sites and interconnected by a communication network.

The processes and logic flows described in this disclosure can be performed by one or more programmable processors executing one or more computer programs to perform actions by operating on input data and generating output. The processes and logic flows can also be performed by, and apparatus can also be implemented as, special purpose logic circuitry, e.g., an FPGA, or an ASIC.

Processors suitable for the execution of a computer program include, by way of example, both general and special purpose microprocessors, and any one or more processors of any kind of digital computer. Generally, a processor will receive instructions and data from a read-only memory, or a random-access memory, or both. Elements of a computer can include a processor configured to perform actions in accordance with instructions and one or more memory devices for storing instructions and data.

Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), or a portable storage device (e.g., a universal serial bus (USB) flash drive), to name just a few.

Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this specification can be implemented with a computer and/or a display device, e.g., a VR/AR device, a head-mount display (HMD) device, a head-up display (HUD) device, smart eyewear (e.g., glasses), a CRT (cathode-ray tube), LCD (liquid-crystal display), OLED (organic light emitting diode), TFT (thin-film transistor), plasma, other flexible configuration, or any other monitor for displaying information to the user and a keyboard, a pointing device, e.g., a mouse, trackball, etc., or a touch screen, touch pad, etc., by which the user can provide input to the computer.

The features disclosed herein may be implemented as part of a smart home or a smart office design, which may implement individually or integrally various electronic devices in a home or office. For example, control or display functions described above may be realized on a mobile terminal such as a smart phone, or on a smart television Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

While this specification contains many specific implementation details, these should not be construed as limitations on the scope of any claims, but rather as descriptions of features specific to particular implementations. Certain features that are described in this specification in the context of separate implementations can also be implemented in combination in a single implementation. Conversely, various features that are described in the context of a single implementation can also be implemented in multiple implementations separately or in any suitable subcombination.

Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Therefore, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking or parallel processing may be utilized.

It is intended that the specification and embodiments be considered as examples only. Other embodiments of the disclosure will be apparent to those skilled in the art in view of the specification and drawings of the present disclosure. That is, although specific embodiments have been described above in detail, the description is merely for purposes of illustration. It should be appreciated, therefore, that many aspects described above are not intended as required or essential elements unless explicitly stated otherwise.

Various modifications of, and equivalent acts corresponding to, the disclosed aspects of the example embodiments, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

The invention claimed is:

1. A sample transport method, applied to a test instrument including a conveyor belt, and a loading platform and a grab position sequentially disposed along a transport direction of the conveyor belt, wherein a plurality of sample holder transport positions are disposed on the conveyor belt, the method including:
   pushing a first sample holder from the loading platform to one of the plurality of sample holder transport positions on the conveyor;
   when a sample position on the first sample holder moves to the grab position, determining whether the sample position moved to the grab position is a target sample position, wherein the target sample position is used to determine whether it is needed to push a next sample holder on the conveyor belt;
   if the sample position moved to the grab position is the target sample position, then determining whether all sample positions on the first sample holder before the target sample position other than a predetermined number of sample positions have completed testing, wherein the predetermined number is a sample position number corresponding to a delay time in outputting information indicating whether a sample needs to be retested;
   if all sample positions on the first sample holder before the target sample position other than the predetermined number of sample positions have completed testing, then determining whether the next sample holder is present on the loading platform; and
   if the next sample holder is present on the loading platform, then pushing the next sample holder from the loading platform to a next sample holder transport position of the conveyor belt;
   wherein said determining whether the sample position moved to the grab position is a target sample position comprises:
   based on a number of sample positions that can be accommodated on the sample holder, a number of sample positions between the loading platform and the grab position, and the predetermined number, obtaining a target sample position numbering of the target sample position on the sample holder; and
   based on a position numbering of the sample position moved to the grab position and the target position numbering, determining whether the sample position moved to the grab position is the target sample position.

2. The method of claim 1, wherein said based on the number of sample positions that can be accommodated on the sample holder, the number of sample positions between the loading platform and the grab position, and the predetermined number, obtaining the target sample position numbering of the target sample position on the sample holder comprises:
   calculating the target position numbering m of the target sample position on the sample holder by using a formula:

$$m = n - j + a - 1$$

where n is the number of sample positions that can be accommodated on the sample holder, and j is a number of sample positions between an end of loading platform toward the grab position and the grab position, a is the predetermined number, wherein m and n are positive integers, j and a are integers greater than or equal to 0, and m satisfies: $0 < m \leq n$.

3. The method of claim 1, wherein said determining whether all sample positions on the first sample holder before the target sample position other than a predetermined number of sample positions have completed testing comprises:
   if all the sample positions on the first sample holder before the target sample position other than a predetermined number of sample positions do not need to be retested or have no sample, then all the sample positions on the first sample holder before the target sample position other than a predetermined number of sample positions have completed testing;
   if any one of the sample positions on the first sample holder before the target sample position other than a predetermined number of sample positions does not satisfy a condition of no need for retesting or having no sample, then not all the sample positions on the first sample holder before the target sample position other than a predetermined number of sample positions have completed testing.

4. A sample transport method, applied to a test instrument including a conveyor belt, and a loading platform and a grab position sequentially disposed along a transport direction of the conveyor belt, wherein a plurality of sample holder transport positions are disposed on the conveyor belt, the method including:
   pushing a first sample holder from the loading platform to one of the plurality of sample holder transport positions of the conveyor;
   when a sample position on the first sample holder moves to the grab position, determining whether the sample position moved to the grab position is a target sample position, wherein the target sample position is used to determine whether it is needed to push a next sample holder on the conveyor belt;
   if the sample position moved to the grab position is the target sample position, then determining whether all sample positions on the first sample holder before the target sample position other than a predetermined number of sample positions have completed testing, wherein the predetermined number is a sample position number corresponding to a delay time in outputting information indicating whether a sample needs to be retested;
   if all sample positions on the first sample holder before the target sample position other than the predetermined number of sample positions have completed testing, then determining whether the next sample holder is present on the loading platform; and
   if the next sample holder is present on the loading platform, then pushing the next sample holder from the loading platform to a next sample holder transport position of the conveyor belt;
   wherein after said determining whether the sample position moved to the grab position is the target sample position, the method further comprises:
   pausing a movement of the conveyor belt, and grabbing a first sample at the target sample position for testing, until completion of grabbing the first sample, then resuming belt movement; and
   when the first sample completes testing and the target sample position moves to the grab position, pausing the belt, until the first sample is returned to the target sample position, then resuming movement of the conveyor belt.

5. The method of claim 4, wherein said pushing the next sample holder from the loading platform to the next sample holder transport position of the conveyor comprises:
in a time period after completion of a grabbing operation of the first sample and before an operation of returning the first sample is started, or in a time period after completion of the operation of the returning the first sample and before the conveyor belt resumes the movement, pushing the next sample holder from the loading platform to the next sample holder transport position on the conveyor belt.

6. The method of claim 4, wherein after the first sample completes testing, the method further includes:
receiving a test result of the first sample;
determining whether the test result of the first sample is abnormal;
if the test result of the first sample is abnormal, then after a current sample testing is completed, moving the first sample back to the grab position to retest the first sample.

7. The method of claim 1, wherein said pushing the next sample holder from the loading platform to the next sample holder transport position of the conveyor belt comprises:
determining whether the next sample holder transport position is located at an exit position of the loading platform;
if the next sample holder transport position is not located at the exit location of the loading platform, then the next sample holder transport position is moved to the exit position of the loading platform, and from the loading platform the next sample holder is pushed onto the next sample holder transport position of the conveyor belt.

8. The method of claim 1, wherein the test instrument further comprises an unloading platform disposed along the transport direction after the grab position; the method further comprises, after said pushing the first sample holder to the one of the plurality of sample holder transport positions on the conveyor belt from the loading platform:
determining whether all samples on the first sample holder have completed testing;
if all the samples on the first sample holder have completed testing, then moving the first sample holder to an entrance location of the unloading platform and transferring the first sample holder from the conveyor belt to the unloading platform.

9. The method of claim 8, wherein after all samples on the first sample holder have completed testing, the method further includes:
determining whether a next sample holder is present on the conveyor belt;
if the next sample holder is present on the conveyor, proceed to testing of each sample position on the next sample holder, and during the testing of each sample on the next sample holder, when the first sample holder moves to the entrance location of the unloading platform, moving the first sample holder from the conveyor belt to the unloading platform.

10. The method of claim 9, wherein after the first sample holder is moved to the unloading platform from the conveyor, the method further includes:
updating a numbering of the next sample holder to the first sample holder.

11. The method of claim 1, wherein said test instrument further comprises, disposed along the transport direction of the conveyor belt between the loading platform and the unloading platform, a preprocessing position, and the method further includes:
obtaining information on the first sample holder when the first sample holder moves to the preprocessing position to thereby guide a grabbing operation at the grab position;
determining whether a sample exists at the sample position on the first sample holder when the first sample holder moves to the preprocessing position; and
if there is a sample at the sample position on the first sample holder, then obtaining basic information required for the testing of the sample.

12. A sample transport method, applied to a test instrument including a conveyor belt, and a loading platform and a grab position sequentially disposed along a transport direction of the conveyor belt, wherein a plurality of sample holder transport positions are disposed on the conveyor belt, the method including:
pushing a first sample holder from the loading platform to one of the plurality of sample holder transport positions of the conveyor;
when a sample position on the first sample holder moves to the grab position, determining whether the sample position moved to the grab position is a target sample position, wherein the target sample position is used to determine whether it is needed to push a next sample holder on the conveyor belt;
if the sample position moved to the grab position is the target sample position, then determining whether all sample positions on the first sample holder before the target sample position other than a predetermined number of sample positions have completed testing, wherein the predetermined number is a sample position number corresponding to a delay time in outputting information indicating whether a sample needs to be retested;
if all sample positions on the first sample holder before the target sample position other than the predetermined number of sample positions have completed testing, then determining whether the next sample holder is present on the loading platform; and
if the next sample holder is present on the loading platform, then pushing the next sample holder from the loading platform to a next sample holder transport position of the conveyor belt;
wherein the test instrument further comprises a motor configured to drive the conveyor belt, the method further includes:
based on a received motor resetting start command, controlling the motor to drive forward in a first direction until a blocker triggers a position limit sensor for a first time, wherein the blocker is disposed on the conveyor belt;
if the position limit sensor that is triggered by the blocker for the first time is a first position limit sensor that is one of a plurality of position limit sensors or a single position limit sensor, controlling the motor to drive forward in the first direction until the first position limit sensor is not triggered; and
controlling the motor to drive at a first speed less than a preset threshold speed opposite to the first direction, until the blocker triggers the first position limit sensor, the motor stops driving, thereby completing resetting.

13. The method of claim 12, further comprising:
if the position limit sensor triggered by the blocker for the first time is not the first position limit sensor, based on a positional relationship between the position limit sensor triggered by the blocker for the first time and the first position limit sensor, controlling the motor until the blocker triggers the first position limit sensor;
controlling the motor to drive forward in the first direction until the first position limit sensor is not triggered; and
controlling the motor to drive opposite to the first direction at the first speed until the blocker triggers the first position limit sensor, and then the motor stops driving.

14. The method of claim 13, wherein said based on the positional relationship between the position limit sensor triggered for the first time and the first position limit sensor, controlling the motor until the blocker triggers the first position limit sensor comprises:
if the first position limit sensor is located in a direction forward of the first direction from the first triggered position limit sensor as a starting point, controlling the motor to drive forward in the first direction until the blocker triggers the first position limit sensor;
if the first position limit sensor is located in a direction opposite to the first direction from the first triggered position limit sensor as a starting point, controlling the motor to drive in a opposite direction of the first direction until the blocker triggers the first position limit sensor.

15. The method of claim 12, wherein said controlling the motor to drive at a first speed less than a preset threshold speed opposite to the first direction comprises:
controlling the motor to accelerate to the first speed, and at the first speed and at a constant speed in a direction opposite to the first direction.

16. The method of claim 12, further comprising:
determining when the motor completes resetting, a position of the blocker is a first position;
receiving the motor resetting start command again, based on the again received motor resetting start command, determining that a position of the blocker is a second position when the motor completes the resetting again; and
adjusting the first speed, according to a position difference between the first position and the second position, such that the position difference is smaller than a position difference threshold.

17. A sample transport device for a test instrument implementing the method according to claim 1, comprising the conveyor belt and the loading platform, and an unloading platform disposed along the transport direction and located after the grab position.

18. The device of claim 17, wherein:
the conveyor belt has a plurality of protrusions disposed uniformly, and a portion between two adjacent protrusions forms each of the plurality of sample holder transport positions; and
a width of each of the plurality of sample holder transport positions is less than or equal to an exit width of the loading platform.

19. The device of claim 18, further comprising:
a motor configured to drive the conveyor belt; and
a controller configured to:
based on a received motor resetting start command, control the motor to drive forward in a first direction until a blocker triggers a position limit sensor for a first time, wherein the blocker is disposed on the conveyor belt;
if the position limit sensor that is triggered by the blocker for the first time is a first position limit sensor that is one of a plurality of position limit sensors or a single position limit sensor, control the motor to drive forward in the first direction until the first position limit sensor is not triggered; and
control the motor to drive at a first speed less than a preset threshold speed opposite to the first direction, until the blocker triggers the first position limit sensor, the motor stops driving, thereby completing resetting.

* * * * *